US007318923B2

(12) United States Patent
Tsurushita et al.

(10) Patent No.: US 7,318,923 B2
(45) Date of Patent: Jan. 15, 2008

(54) HUMANIZED ANTI-β ANTIBODIES

(75) Inventors: Naoya Tsurushita, Palo Alto, CA (US);
Maximiliano J. Vasquez, Palo Alto, CA (US)

(73) Assignee: Eli Lilly and Company, Indianapolis, IN (US)

( * ) Notice: Subject to any disclaimer, the term of this patent is extended or adjusted under 35 U.S.C. 154(b) by 627 days.

(21) Appl. No.: 10/476,265

(22) PCT Filed: Apr. 26, 2002

(86) PCT No.: PCT/US02/11853

§ 371 (c)(1),
(2), (4) Date: Oct. 22, 2003

(87) PCT Pub. No.: WO02/088306

PCT Pub. Date: Nov. 7, 2002

(65) Prior Publication Data
US 2005/0090648 A1   Apr. 28, 2005

Related U.S. Application Data

(60) Provisional application No. 60/287,539, filed on Apr. 30, 2001.

(51) Int. Cl.
*A61K 39/395* (2006.01)
*C12P 21/08* (2006.01)
*C07K 16/18* (2006.01)
*C07H 21/04* (2006.01)
*C12N 5/16* (2006.01)

(52) U.S. Cl. ............... 424/133.1; 530/387.3; 530/387.9; 536/23.53; 435/328; 435/331

(58) Field of Classification Search ............ None
See application file for complete search history.

(56) References Cited

U.S. PATENT DOCUMENTS

| | | | |
|---|---|---|---|
| 5,530,101 A | 6/1996 | Queen et al. | |
| 5,585,089 A | 12/1996 | Queen et al. | |
| 5,589,154 A * | 12/1996 | Anderson | 424/1.41 |
| 5,688,651 A | 11/1997 | Solomon | |
| 5,693,761 A | 12/1997 | Queen et al. | |
| 5,693,762 A | 12/1997 | Queen et al. | |
| 6,180,370 B1 | 1/2001 | Queen et al. | |
| 2003/0165496 A1 | 9/2003 | Basi et al. | |

FOREIGN PATENT DOCUMENTS

| | | |
|---|---|---|
| EP | 613 007 | 8/1994 |
| WO | WO 96/18900 | 6/1996 |
| WO | WO 96/25435 | 8/1996 |
| WO | WO 98/44955 | 10/1998 |
| WO | WO 99/06066 | 2/1999 |
| WO | WO 99/27944 | 6/1999 |
| WO | WO 99/60024 | 11/1999 |
| WO | WO 00/72876 A2 | 12/2000 |
| WO | WO 00/72880 A2 | 12/2000 |
| WO | WO 00/77178 | 12/2000 |
| WO | WO 01/18169 | 3/2001 |
| WO | WO 02/46237 A2 | 6/2002 |

OTHER PUBLICATIONS

Kimchi EY et al. Analysis of cerebral angiopathy in a transgenic mouse model of Alzheimer's disease using in vivo multiphoton microscopy. J. Neuropathol Exp Neurol, 2001; 60(3): 274-279.*
De Felice FG and Ferreira ST. beta-Amyloid production, aggregation, and clearance as targets for therapy in Alzheimer's disease. Cell Mol Neurobiol. 2002; 22(5-6): 545-563.*
Münch G and Robinson SR. Potential neurotoxic inflammatory responses to Abeta vaccination in humans. J Neural Transm, 2002; 109: 1081-1087.*
Small DH et al. Alzheimer's disease and Abeta toxicity: from top to bottom. Nat Rev. Aug. 2001; 2: 595-598.*
De Lustig ES et al. Peripheral markers and diagnostic criteria in Alzheimer's disease: critical evaluations. Rev in Neurosciences, 1994; 5: 213-224.*
Vickers JC. A vaccine against Alzheimer's disease: Developments to date. Drugs Aging, 2002; 19(7): 487-494.*
Jones, PT, et al., "Replacing the complementarity-determining regions in a human antibody with those from a mouse," Nature, vol. 321, pp. 522-525, May 29, 1986.
Frenkel, D, et al, "N-terminal EFRH sequence of Alzheimer's β-amylod peptide represents the epitope of its anti-aggregating antibodies," J. Neuroimmunol., vol. 88, No. 1-2, pp. 85-90, Aug. 1, 1998.
Frenkel, D, et al., "High affinity binding of monoclonal antibodies to the sequential epitope EFRH of β-amyloid peptide is essential for modulation of fibrillar aggregation," J. Neuroimmunol., vol. 95, No. 1-2, pp. 136-142, Mar. 1, 1999.
Parvizi J, et al.,"The Selective Vulnerability of Brainstem Nuclei to Alzheimer's Disease," Ann Neurol., vol. 49, No. 1, pp. 53-66, Jan. 2001.
Seubert, P, et al., "Isolation and quantification of soluble Alzheimer's β-peptide from biological fluids," Nature, vol. 359, pp. 325-327, 1992.
Van Gool, WA, et al., "Concentrations of amyloid-β protein in cerebrospinal fluid increases with age in patients free from neurodegenerative disease," Neuroscience Lett., vol. 172, pp. 122-124 ,1994.

(Continued)

*Primary Examiner*—Eileen B. O'Hara
*Assistant Examiner*—Kimberly A. Ballard
(74) *Attorney, Agent, or Firm*—James J. Kelley; Mark J. Stewart

(57) ABSTRACT

Humanized forms of mouse antibody 3D6 that retain the binding properties of mouse 3D6 are disclosed. Also disclosed are processes for making the humanized antibody, intermediates for making the humanized antibodies, including, nucleotide sequences, vectors, transformed host cells, and methods of using the humanized antibody to treat, prevent, alleviate, reverse, or otherwise ameliorate symptoms or pathology or both, that are associated with Down's syndrome or pre-clinical or clinical Alzheimer's disease or cerebral amyloid angiopathy.

17 Claims, No Drawings

OTHER PUBLICATIONS

Tabaton, M, el al., "Soluble Amyloid β-Protein is a Marker of Alzheimer Amyloid in Brain but Not in Cerebrospinal Fluid," Biochemical and Biophysical Research Communications, vol. 200, No. 3, pp. 1598-1603, May 16, 1994.

Walker, L, et al., "Labeling of Cerebral Amyloid In Vivo with a Monoclonal Antibody," J Neuropathol Exp Neurol., vol. 53, No. 4, pp. 377-383, Jul. 1994.

Nitsch, RM, et al., "Cerebrospinal Fluid Levels of Amyloid β-Protein in Alzheimer's Disease: Inverse Correlation with Severity of Dementia and Efect of Apolipoprotein E Genotype," Annals Neurology, vol. 37, pp. 512-518, 1995.

Gomez-Isla, T, et al., A Novel Presenilin-1 Mutation: Increased β-Amyloid and Neurofibrillary Changes, Annals Neurology, vol. 41, pp. 809-813, 1997.

Schenk, D, et al., "Immunization with amyloid-β attenuates Alzheimer-disease-like pathology in the PDAPP mouse," *Nature*, vol. 400, pp. 173-177, 1999.

Bard, F, et al., "Antibodies against Abeta reduce Amyloid Burden In Vivo," Society for Neuroscience Abstracts, Vol. p. 1059, Nov. 4, 2000.

Bard, F, et al., "Peripherally administered antibodies against amyloid beta-peptide enter the central nervous system and reduce pathology in a mouse model of Alzheimer disease," *Nature Med.*, vol. 6, No. 8, pp. 916-919, 2000.

Chothia, C, et al., "Canonical Structures for the Hypervariable Regions of Immunoglobulins," *J. Mol. Biol*, vol. 196, pp. 901-917, 1987.

Chothia, C, et al., et al., "Conformations of imunoglobulin hypervariable regions," *Nature*, vol. 342, pp. 878-883, Dec. 21-28, 1989.

Queen, et al., "A humanized antibody that binds to the interleukin 2 receptor," *Proc. Natl. Acad. Sci. USA*, vol. 86, pp. 10029-10033, Dec. 1989.

Co, MS, et al., "Humanized antibodies for antiviral therapy," *Proc. Natl. Acad. Sci. USA*, vol. 88, pp. 2869, Apr. 1991.

Remington's Pharmaceutical Sciences, 18th Edition, Mack Publishing Co., Easton PA, pp. 1481-1498, 1504-1512, and 1519-1580, 1990.

Hyman, B., et al., "Kunitz Protease Inhibitor-Containing Amyloid β Protein Precursor Immunoreactivity in Alzheimer's disease," *J. Neuropath. Exp. Neurol.*, vol. 51, No. 1, pp. 76-83, Jan. 1992.

Walker, L, et al.,"Labeling of β-Amyloid In Vivo," (Abstract) Neurobiol. Aging, vol. 13, Supl. 1, S23, 1992.

Hanan, E, et al., "Inhibitory Effect of Monoclonal Antibodies on Alzheimer'β-Amyloid Peptide Aggregation" *Int. J. Exp. Clin. Invest.*, vol. 3, pp. 130-133, 1996.

Solomon, B, et al., "Monoclonal antibodies inhibit n vitro fibrillar aggregation of the Alzheimer beta-amyloid peptide," *Proc Natl Acad Sci U S A.*, vol. 93, No. 1, pp. 452-455, Jan. 1996.

Friedland, RP, et al., "Neuroimaging of Vessel Amyloid in Alzheimer's Disease," Ann. NY Acad. Science, 826, pp. 242-247, 1997.

Goldman, DL, et al., "Pharmacokinetics and Biodistribution of a Monoclonal Antibody to Cryptococcus Neoformans Capsular Polysaccharide Antigen . . . ," *Journal of Medical & Veterinary Mycology*, vol. 35, pp. 271-278, 1997.

Solomon, B, et al., "Disaggregation of Alzheimer β-amyloid by site-directed mAb," *Proc. Natl. Acad. Sci.,*, vol. 94, pp. 4109-4112, 1997.

St. George-Hyslop, P, et al., "Antibody clears senile plaques," *Nature*, vol. 400, pp. 116-117, Jul. 8, 1999.

Blass, JP, "Immunologic Treatment of Alzheimer's Disease," *New Engl. J. Med.* vol. 341, No. 22, pp. 1694-1695, Nov. 25, 1999.

Schenk, D, et al., "A possible vaccine for treatment of AD," World Alzheimer's Congress 2000, Plenary Session III, 605, Washington, D.C., Jul. 11, 2000.

Bacskai BJ, et al., "Imaging of amyloid-â deposits in brains of living mice permits direct observation of clearance of plaques with immunotherapy," Nature Medicine vol. 7, No. 3, pp. 369-372, Mar. 2001.

Simmons, L, et al., "Secondary Structure of Amyloid β Peptide Correlates with Neurotoxic Activity In Vitro," *Molecular Pharmacology*, vol. 45, pp. 373-379, 1994.

Arendash, GW, et al., "Behavioral Assessment of Alzheimer's Transgenic Mice Following Long-Term Aβ Vaccination: Task Specificity and Correlations between Aβ Deposition and Spatial Memory," *DNA and Cell Biology*, vol. 20, No. 11, pp. 737-744, 2001.

DeMattos, RB, et al., "Peripheral anti-Aβ antibody alters CNS and plasma Aβ clearance and decreases brain Aβ burden in a mouse model of Alzheimer's disease," *PNAS*, vol. 98, No. 15, pp. 8850-8855, 2001.

Dickey, CA, et al., "Duration and Specificity of Humoral Immune Responses in Mice Vaccinated with the Alzheimer's Disease-Associated β-Amyloid 1-42 Peptide," *DNA and Cell Biology*, vol. 20, No. 11, pp. 723-729, 2001.

Esiri, MM, et al, "Is an effective immune intervention for Alzheimer's disease in prospect?" *Trends Pharmacol Sci,*, vol. 22, No. 1, pp. 2-3, 2001.

Haass C, et al, "Protofibrils, the unifying toxic molecule of neurodegenerative disorders?" *Nature Neurosciences*, vol. 4, No. 9, pp. 219-224, Sep. 2001.

Ruker, F, et al., "Expression of a Human Monoclonal Anti-HIV-1 Antibody in CHO Cells," Ann. N.Y. Acad. Sci., vol. 646, pp. 212-219, Dec. 27, 1991.

Masliah E, et al., "Comparison of Neurodegenerative Pathology in Transgenic Mice Overexpressing V717F β-Amyloid Precursor Protein and Alzheimer's Disease," J. Neurosci., vol. 16, No. 18, pp. 5795-5811, Sep. 15, 1996.

Vanderstichele H, et al., "Development of a Specific Diagnostic Test for Measurement of β-Amyloid (1-42) [βA4(1-42)] in CSF," Adv. Behav. Biol., pp. 773-778 (1998).

Johnson-Wood K, et al., "Amyloid precursor protein processing and Aβ-42 deposition in a transgenic mouse model of Alzheimer disease," PNAS 94:1550-1555 (1997).

* cited by examiner

HUMANIZED ANTI-β ANTIBODIES

This application claims priority of International Application No. US02/11853, filed Apr. 26, 2002, which claims the priority of U.S. provisional application No. 60/287,539, filed Apr. 30, 2001. The contents of each of these applications is incorporated herein by reference.

The invention relates to humanized antibodies useful for treating and preventing human diseases associated with amyloid β (Aβ), such as Alzheimer's disease, Down's syndrome, and cerebral amyloid angiopathy. Mouse monoclonal antibody 3D6 has been widely used in analytical methods. After 3D6 was administered to a group of 11.5-12 month-old heterozygous, transgenic PDAPP mice ($APP^{V717F}$) at a weekly intraperitoneal dose of about 10 mg/kg for six months, it has been reported that the mice had significantly reduced plaque burden, although the specific location of the reduction was not disclosed. [Bard, F., et al., *Nature Med.* 6:916-919 (2000); WO 00/72876 and WO 00/72880, 7 Dec., 2000]. It was asserted that the antibody gained access to the central nervous system in sufficient amounts to "decorate" β-amyloid plaques. Finally, it was stated that mouse 3D6 induces phagocytosis of amyloid plaques in in vitro studies.

Methods for administering aggregated Aβ1-42 to provoke an immunologic response and reduced amyloid deposits are described in PCT publication WO99/27944, published 10 Jun. 1999. The description postulates that full-length aggregated Aβ peptide would be a useful immunogen. The application also indicates that antibodies that bind to Aβ peptide could be used as alternate therapeutic agents. However, this appears to be speculation since the supporting data reflect protocols that involve active immunization using, for example, Aβ1-42.

WO 99/60024, published 25 Nov. 1999, is directed to methods for amyloid removal using anti-amyloid antibodies. The mechanism, however, is stated to utilize the ability of anti-Aβ antibodies to bind to pre-formed amyloid deposits (i.e. plaques) and result in subsequent microglial clearance of localized plaques. This mechanism was not proved in vivo. This publication further states that to be effective against Aβ plaques, anti-Aβ antibodies must be delivered directly to the brain, because antibodies cannot cross the blood brain barrier.

Queen, et al. describe methods of humanizing antibodies [e.g., U.S. Pat. Nos. 5,585,089, 5,693,761, 5,693,762, 6,180,370].

Humanized forms of 3D6 are needed for use in humans having Down's syndrome, or pre-clinical or clinical Alzheimer's disease or cerebral amyloid angiopathy (CAA). However, it is not known whether 3D6 can be humanized so that the humanized antibody retained the binding properties of the mouse antibody.

SUMMARY OF THE INVENTION

This invention provides humanized forms of 3D6. These humanized antibodies have binding properties (affinity and epitope location) that are approximately the same as those of the mouse 3D6 antibody. The invention includes antibodies, single chain antibodies, and fragments thereof. The invention includes antibodies wherein the CDR are those of mouse monoclonal antibody 3D6 (sequences SEQ ID NO:1 through SEQ ID NO:6) and wherein the antibodies retain approximately the binding properties of the mouse antibody and have in vitro and in vivo properties functionally equivalent to the mouse antibody. In another aspect, this invention provides humanized antibodies and fragments thereof, wherein the variable regions have sequences comprising the CDR from mouse antibody 3D6 and specific human framework sequences (sequences SEQ ID NO:7-SEQ ID NO:10), wherein the antibodies retain approximately the binding properties of the mouse antibody and have in vitro and in vivo properties functionally equivalent to the mouse antibody 3D6. In another aspect, this invention provides humanized antibodies and fragments thereof, wherein the light chain is SEQ ID NO:11 and the heavy chain is SEQ ID NO:12.

Also part of the invention are polynucleotide sequences that encode the humanized antibodies or fragments thereof disclosed above, vectors comprising the polynucleotide sequences encoding the humanized antibodies or fragments thereof, host cells transformed with the vectors or incorporating the polynucleotides that express the humanized antibodies or fragments thereof, pharmaceutical formulations of the humanized antibodies and fragments thereof disclosed herein, and methods of making and using the same.

Such humanized antibodies and fragments thereof are useful for, among other things, treating and preventing diseases and conditions characterized by Aβ plaques or Aβ toxicity in the brain, such as Alzheimer's disease, Down's syndrome, and cerebral amyloid angiopathy in humans.

The invention also includes use of a humanized antibody of the present invention for the manufacture of a medicament, including prolonged expression of recombinant sequences of the antibody or antibody fragment in human tissues, for treating, preventing, or reversing Alzheimer's disease, Down's syndrome, or cerebral amyloid angiopathy, or to inhibit the formation of amyloid plaques or the effects of toxic soluble Aβ species in humans.

DETAILED DESCRIPTION OF THE INVENTION

We have surprisingly found that humanized antibodies, wherein the CDRs originate from mouse monoclonal antibody 3D6 and the framework and other portions of the antibodies originate from a human germ line, bind Aβ1-40 and Aβ1-42 with at least the affinity with which mouse 3D6 binds Aβ. Thus, we have a reasonable basis for believing that humanized antibodies of this specificity, modified to reduce their immunogenicity by converting them to a humanized form, offer the opportunity to treat, both prophylactically and therapeutically, conditions in humans that are associated with formation of beta-amyloid plaques. These conditions include, as noted above, pre-clinical and clinical Alzheimer's, Down's syndrome, and pre-clinical and clinical cerebral amyloid angiopathy.

As used herein, the word "treat" includes therapeutic treatment, where a condition to be treated is already known to be present and prophylaxis—i.e., prevention of, or amelioration of, the possible future onset of a condition.

By "antibody" is meant a monoclonal antibody per se, or an immunologically effective fragment thereof, such as an Fab, Fab', or $F(ab')_2$ fragment thereof. In some contexts, herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" are single chain forms. Preferably, but not necessarily, the antibodies useful in the invention are produced recombinantly. Antibodies may or may not be glycosylated, though glycosylated antibodies are preferred. Antibodies are properly cross-linked via disulfide bonds, as is well known.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as kappa and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 3 or more amino acids.

The variable regions of each light/heavy chain pair form the antibody binding site. Thus, an intact antibody has two binding sites. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with well known conventions [Kabat "Sequences of Proteins of Immunological Interest" National Institutes of Health, Bethesda, Md., 1987 and 1991; Chothia, et al., J. Mol. Biol. 196:901-917 (1987); Chothia, et al., Nature 342:878-883 (1989)].

By "humanized antibody" is meant an antibody that is composed partially or fully of amino acid sequences derived from a human antibody germline by altering the sequence of an antibody having non-human complementarity determining regions (CDR). A humanized immunoglobulin does not encompass a chimeric antibody, having a mouse variable region and a human constant region. However, the variable region of the antibody and even the CDR are humanized by techniques that are by now well known in the art. The framework regions of the variable regions are substituted by the corresponding human framework regions leaving the non-human CDR substantially intact. As mentioned above, it is sufficient for use in the methods of the invention, to employ an immunologically specific fragment of the antibody, including fragments representing single chain forms.

Humanized antibodies have at least three potential advantages over non-human and chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC).

2) The human immune system should not recognize the framework or C region of the humanized antibody as foreign, and therefore the antibody response against such an injected antibody should be less than against a totally foreign non-human antibody or a partially foreign chimeric antibody.

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

The design of humanized immunoglobulins may be carried out as follows. As to the human framework region, a framework or variable region amino acid sequence of a CDR-providing non-human immunoglobulin is compared with corresponding sequences in a human immunoglobulin variable region sequence collection, and a sequence having a high percentage of identical amino acids is selected. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model [Queen, et al., Proc. Natl. Acad. Sci. USA 86:10029-10033 (1989), and Co, et al., Proc. Natl. Acad. Sci. USA 88, 2869 (1991)]. When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position.

A preferred humanized antibody is a humanized form of mouse antibody 3D6. The CDRs of humanized 3D6 have the following amino acid sequences: light chain CDR1:

```
 1               5
Lys Ser Ser Gln Ser Leu Leu Asp         (SEQ ID NO:1)

10                  15
Ser Asp Gly Lys Thr Tyr Leu Asn
``` light chain CDR2:

```
 1               5
Leu Val Ser Lys Leu Asp Ser             (SEQ ID NO:2)
``` light chain CDR3:

```
 1               5
Trp Gln Gly Thr His Phe Pro Arg Thr     (SEQ ID NO:3)
``` heavy chain CDR1:

```
 1               5
Asn Tyr Gly Met Ser                     (SEQ ID NO:4)
``` heavy chain CDR2:

```
                1               5
Ser Ile Arg Ser Gly Gly Gly Arg Thr     (SEQ ID NO:5)

10                  15
Tyr Tyr Ser Asp Asn Val Lys Gly
``` and, heavy chain CDR3:

```
                1               5
Tyr Asp His Tyr Ser Gly Ser Ser Asp     (SEQ ID NO:6)

10
Tyr.
```

A preferred light chain variable region of a humanized antibody of the present invention has the following amino acid sequence, in which the framework originated from human germline Vk segment DPK19 and J segment Jk4:

```
                                        (SEQ ID NO:7)
                1               5
        Xaa Val Val Met Thr Gln Xaa Pro 10                  15
        Leu Xaa Leu Pro Val Thr Xaa Gly

20
        Gln Pro Ala Ser Ile Ser Cys Lys 25                  30
        Ser Ser Gln Ser Leu Leu Asp Ser 35                  40
        Asp Gly Lys Thr Tyr Leu Asn Trp

-continued
                    45
        Leu Gln Gln Arg Pro Gly Gln Ser 50                  55
        Pro Xaa Arg Leu Ile Tyr Leu Val 60
        Ser Lys Leu Asp Ser Gly Val Pro 65                  70
        Asp Arg Phe Ser Gly Ser Gly Ser 75                  80
        Gly Thr Asp Phe Thr Leu Lys Ile 85
        Ser Arg Val Glu Ala Glu Asp Xaa 90                  95
        Val Tyr Tyr Cys Trp Gln Gly Thr 100                 105
        His Phe Pro Arg Thr Phe Gly Gly 110
        Gly Thr Lys Xaa Glu Ile Lys Arg
``` wherein:

Xaa at position 1 is Asp or Tyr;

Xaa at position 7 is Ser or Thr;

Xaa at position 10 is Ser or Thr;

Xaa at position 15 is Leu, Ile, or Val;

Xaa at position 50 is Arg or Lys;

Xaa at position 88 is Val or Leu; and

Xaa at position 109 is Val or Leu.

A preferred heavy chain variable region of a humanized antibody of the present invention has the following amino acid sequence, in which the framework originated from human germline VH segment DP-45 and J segment JH4, with several amino acid substitutions to the consensus amino acids in the same human subgroup to reduce potential immunogenicity:

```
              1                   5                   10                  15
        Glu Val Xaa Leu Val Glu Ser Gly Gly Gly Leu Val Gln Pro Gly Gly   (SEQ ID NO:8)

20                  25                  30
        Ser Leu Arg Leu Ser Cys Ala Gly Ser Gly Phe Thr Phe Ser Asn Tyr 35                  40                  45
        Gly Met Ser Trp Val Arg Gln Ala Pro Gly Lys Gly Leu Glu Trp Val 50                  55                  60
        Ala Ser Ile Arg Ser Gly Gly Arg Thr Tyr Tyr Ser Asp Asn Val 65                  70                  75                  80
        Lys Gly Arg Phe Thr Ile Ser Arg Glu Asn Ala Lys Asn Xaa Leu Tyr 85                  90                  95
        Leu Gln Met Asn Ser Leu Xaa Xaa Glu Asp Thr Ala Val Tyr Tyr Cys 100                 105                 110
        Val Arg Tyr Asp His Tyr Ser Gly Ser Ser Asp Tyr Trp Gly Gln Gly

115
        Thr Xaa Val Thr Val Ser Ser
``` wherein:

Xaa at position 3 is Gln, Lys, or Arg;

Xaa at position 78 is Ser or Thr;

Xaa at position 87 is Arg or Lys;

Xaa at position 88 is Ala, Ser, or Thr; and

Xaa at position 114 is Leu, Thr, Ile, or Val.

A particularly preferred light chain variable region of a humanized antibody of the present invention has the following amino acid sequence, in which the framework originated from human germline Vk segment DPK19 and J segment Jk4:

```
 1               5                    10                     15
Asp Val Val Met Thr Gln Ser Pro Leu Ser Leu Pro Val Thr Leu Gly  (SEQ ID NO:9)

20                  25                    30
Gln Pro Ala Ser Ile Ser Cys Lys Ser Ser Gln Ser Leu Leu Asp Ser 35                  40                    45
Asp Gly Lys Thr Tyr Leu Asn Trp Leu Gln Gln Arg Pro Gly Gln Ser 50                  55                    60
Pro Arg Arg Leu Ile Tyr Leu Val Ser Lys Leu Asp Ser Gly Val Pro 65                  70                  75                    80
Asp Arg Phe Ser Gly Ser Gly Ser Gly Thr Asp Phe Thr Leu Lys Ile 85                  90                    95
Ser Arg Val Glu Ala Glu Asp Val Gly Val Tyr Tyr Cys Trp Gln Gly 100                 105                   110
Thr His Phe Pro Arg Thr Phe Gly Gly Gly Thr Lys Val Glu Ile Lys

Arg.
```

A particularly preferred heavy chain variable region of a humanized antibody of the present invention has the following amino acid sequence, in which the framework originated from human germline VH segment DP-45 and J segment JH4:

```
 1               5                    10                     15
Glu Val Gln Leu Val Glu Ser Gly Gly Gly Leu Val Gln Pro Gly Gly  (SEQ ID NO:10)

20                  25                    30
Ser Leu Arg Leu Ser Cys Ala Gly Ser Gly Phe Thr Phe Ser Asn Tyr 35                  40                    45
Gly Met Ser Trp Val Arg Gln Ala Pro Gly Lys Gly Leu Glu Trp Val 50                  55                    60
Ala Ser Ile Arg Ser Gly Gly Gly Arg Thr Tyr Tyr Ser Asp Asn Val 65                  70                  75                    80
Lys Gly Arg Phe Thr Ile Ser Arg Glu Asn Ala Lys Asn Ser Leu Tyr 85                  90                    95
Leu Gln Met Asn Ser Leu Arg Ala Glu Asp Thr Ala Val Tyr Tyr Cys 100                 105                   110
Val Arg Tyr Asp His Tyr Ser Gly Ser Ser Asp Tyr Trp Gly Gln Gly

115
Thr Leu Val Thr Val Ser Ser.
```

A preferred light chain for a humanized antibody of the present invention has the amino acid sequence:

```
 1               5                    10                     15
Asp Val Val Met Thr Gln Ser Pro Leu Ser Leu Pro Val Thr Leu Gly (SEQ ID NO:11}

20                  25                    30
Gln Pro Ala Ser Ile Ser Cys Lys Ser Ser Gln Ser Leu Leu Asp Ser 35                  40                    45
Asp Gly Lys Thr Tyr Leu Asn Trp Leu Gln Gln Arg Pro Gly Gln Ser 50                  55                    60
Pro Arg Arg Leu Ile Tyr Leu Val Ser Lys Leu Asp Ser Gly Val Pro 65                  70                  75                    80
Asp Arg Phe Ser Gly Ser Gly Ser Gly Thr Asp Phe Thr Leu Lys Ile 85                  90                    95
```

```
                            -continued
Ser Arg Val Glu Ala Glu Asp Val Gly Val Tyr Tyr Cys Trp Gln Gly
                100             105             110
Thr His Phe Pro Arg Thr Phe Gly Gly Gly Thr Lys Val Glu Ile Lys
            115             120             135
Arg Thr Val Ala Ala Pro Ser Val Phe Ile Phe Pro Pro Ser Asp Glu
        130             135             140
Gln Leu Lys Ser Gly Thr Ala Ser Val Val Cys Leu Leu Asn Asn Phe
145             150             155             160
Tyr Pro Arg Glu Ala Lys Val Gln Trp Lys Val Asp Asn Ala Leu Gln
                165             170             175
Ser Gly Asn Ser Gln Glu Ser Val Thr Glu Gln Asp Ser Lys Asp Ser
            180             185             190
Thr Tyr Ser Leu Ser Ser Thr Leu Thr Leu Ser Lys Ala Asp Tyr Glu
        195             200             205
Lys His Lys Val Tyr Ala Cys Glu Val Thr His Gln Gly Leu Ser Ser
    210             215
Pro Val Thr Lys Ser Phe Asn Arg Gly Glu Cys.
```

A preferred heavy chain for a humanized antibody of the present invention has the amino acid sequence:

```
  1               5                   10                  15
Gln Val Gln Leu Val Gln Ser Gly Gly Gly Leu Val Gln Pro Gly Gly   (SEQ ID NO:12)
                20                  25                  30
Ser Leu Arg Leu Ser Cys Ala Gly Ser Gly Phe Thr Phe Ser Asn Tyr
            35                  40                  45
Gly Met Ser Trp Val Arg Gln Ala Pro Gly Lys Gly Leu Glu Trp Val
        50                  55                  60
Ala Ser Ile Arg Ser Gly Gly Gly Arg Thr Tyr Tyr Ser Asp Asn Val
 65                  70                  75                  80
Lys Gly Arg Phe Thr Ile Ser Arg Glu Asn Ala Lys Asn Ser Leu Tyr
                85                  90                  95
Leu Gln Met Asn Ser Leu Arg Ala Glu Asp Thr Ala Val Tyr Tyr Cys
                100             105             110
Val Arg Tyr Asp His Tyr Ser Gly Ser Ser Asp Tyr Trp Gly Gln Gly
            115             120             125
Thr Leu Val Thr Val Ser Ser Ala Ser Thr Lys Gly Pro Ser Val Phe
        130             135             140
Pro Leu Ala Pro Ser Ser Lys Ser Thr Ser Gly Gly Thr Ala Ala Leu
145             150             155             160
Gly Cys Leu Val Lys Asp Tyr Phe Pro Gln Pro Val Thr Val Ser Trp
                165             170             175
Asn Ser Gly Ala Leu Thr Ser Gly Val His Thr Phe Pro Ala Val Leu
            180             185             190
Gln Ser Ser Gly Leu Tyr Ser Leu Ser Ser Val Val Thr Val Pro Ser
        195             200             205
Ser Ser Leu Gly Thr Gln Thr Tyr Ile Cys Asn Val Asn His Lys Pro
    210             215             220
Ser Asn Thr Lys Val Asp Lys Lys Val Glu Pro Lys Ser Cys Asp Lys
225             230             235             240
Thr His Thr Cys Pro Pro Cys Pro Ala Pro Gln Leu Leu Gly Gly Pro
                245             250             255
Ser Val Phe Leu Phe Pro Pro Lys Pro Lys Asp Thr Leu Met Ile Ser
```

```
             260                 265                 270
Arg Thr Pro Glu Val Thr Cys Val Val Val Asp Val Ser His Glu Asp 275                 280                 285
Pro Glu Val Lys Phe Asn Trp Tyr Val Asp Gly Val Glu Val His Asn 290                 295                 300
Ala Lys Thr Lys Pro Arg Glu Glu Gln Tyr Asn Ser Thr Tyr Arg Val 305                 310                 315                 320
Val Ser Val Leu Thr Val Leu His Gln Asp Trp Leu Asn Gly Lys Glu 325                 330                 335
Tyr Lys Cys Lys Val Ser Asn Lys Ala Leu Pro Ala Pro Ile Glu Lys 340                 345                 350
Thr Ile Ser Lys Ala Lys Gly Gln Pro Arg Glu Pro Gln Val Tyr Thr 355                 360                 365
Leu Pro Pro Ser Arg Asp Glu Leu Thr Lys Asn Gln Val Ser Leu Thr 370                 375                 380
Cys Leu Val Lys Gly Phe Tyr Pro Ser Asp Ile Ala Val Glu Trp Glu 385                 390                 395                 400
Ser Asn Gly Gln Pro Glu Asn Asn Tyr Lys Thr Thr Pro Pro Val Leu 405                 410                 415
Asp Ser Asp Gly Ser Phe Phe Leu Tyr Ser Lys Leu Thr Val Asp Lys 420                 425                 430
Ser Arg Trp Gln Gln Gly Asn Val Phe Ser Cys Ser Val Met His Glu 435                 440                 445
Ala Leu His Asn His Tyr Thr Gln Lys Ser Leu Ser Leu Ser Pro Gly

Lys
```

Other sequences are possible for the light and heavy chains for humanized 3D6. The immunoglobulins can have two pairs of light chain/heavy chain complexes, at least one chain comprising one or more mouse complementarity determining regions functionally joined to human framework region segments.

In another aspect, the present invention is directed to recombinant polynucleotides encoding antibodies which, when expressed, comprise the heavy and light chain CDRs from an antibody of the present invention. Exemplary polynucleotides, which on expression code for the polypeptide chains comprising the heavy and light chain CDRs of monoclonal antibody 3D6 are given herein. Due to codon degeneracy, other polynucleotide sequences can be readily substituted for those sequences. Particularly preferred polynucleotides of the present invention encode antibodies, which when expressed, comprise the CDRs of SEQ ID NO:1-SEQ ID NO:6, or any of the variable regions of SEQ ID NO:7-SEQ ID NO:10, or the light and heavy chains of SEQ ID NO:11 and SEQ ID NO:12.

The polynucleotides will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host cell line, the host cell is propagated under conditions suitable for expressing the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), using any of a variety of well known techniques. Joining appropriate genomic and synthetic sequences is a common method of production, but cDNA sequences may also be utilized.

Below is a cDNA sequence (SEQ ID NO:17), from which the light chain having the amino acid sequence of SEQ ID NO:19 may be expressed.

```
   ATGATGAGTCCTGCCCAGTTCCTGTTTCTGTTAGTGCTCTGGATTCGGGAAACCAACGGT
 1 ---------+---------+---------+---------+---------+---------+   60
    M  M  S  P  A  Q  F  L  F  L  L  V  L  W  I  R  E  T  N  G

GATGTTGTGATGACCCAGTCTCCACTCTCCTTGCCTGTTACCCTGGGACAACCAGCCTCC
61 ---------+---------+---------+---------+---------+---------+  120
    D  V  V  M  T  Q  S  P  L  S  L  P  V  T  L  G  Q  P  A  S
```

-continued

```
    ATCTCTTGCAAGTCAAGTCAGAGCCTCTTAGATAGTGATGGAAAGACATATTTGAATTGG
121 ---------+---------+---------+---------+---------+---------+ 180
     I  S  C  K  S  S  Q  S  L  L  D  S  D  G  K  T  Y  L  N  W

TTGCAACAGCGCCCAGGCCAGTCTCCAAGACGCCTAATCTATCTGGTGTCTAAACTGGAC
181 ---------+---------+---------+---------+---------+---------+ 240
     L  Q  Q  R  P  G  Q  S  P  R  R  L  I  Y  L  V  S  K  L  D

TCTGGAGTCCCTGACAGGTTCTCTGGCAGTGGATCAGGGACAGATTTTACACTGAAAATC
241 ---------+---------+---------+---------+---------+---------+ 300
     S  G  V  P  D  R  F  S  G  S  G  S  G  T  D  F  T  L  K  I

AGCAGAGTCGAGGCTGAGGATGTGGGAGTTTATTATTGCTGGCAAGGTACACATTTTCCT
301 ---------+---------+---------+---------+---------+---------+ 360
     S  R  V  E  A  E  D  V  G  V  Y  Y  C  W  Q  G  T  H  F  P

CGGACGTTCGGTGGAGGCACCAAGGTGGAAATCAAACGTACTGTGGCTGCACCATCTGTC
361 ---------+---------+---------+---------+---------+---------+ 420
     R  T  F  G  G  G  T  K  V  E  I  K  R  T  V  A  A  P  S  V

TTCATCTTCCCGCCATCTGATGAGCAGTTGAAATCTGGAACTGCCTCTGTTGTGTGCCTG
421 ---------+---------+---------+---------+---------+---------+ 480
     F  I  F  P  P  S  D  E  Q  L  K  S  G  T  A  S  V  V  C  L

TCGAATAACTTCTATCCCAGAGAGGCCAAAGTACAGTGGAAGGTGGATAACGCCCTCCAA
481 ---------+---------+---------+---------+---------+---------+ 540
     L  N  N  F  Y  P  R  E  A  K  V  Q  W  K  V  D  N  A  L  Q

TCGGGTAACTCCCAGGAGAGTGTCACAGAGCAGGACAGCAAGGACAGCACCTACAGCCTC
541 ---------+---------+---------+---------+---------+---------+ 600
     S  G  N  S  Q  E  S  V  T  E  Q  D  S  K  D  S  T  Y  S  L

AGCAGCACCCTGACGCTGAGCAAAGCAGACTACGAGAAACACAAAGTCTACGCCTGCGAA
601 ---------+---------+---------+---------+---------+---------+ 660
     S  S  T  L  T  L  S  K  A  D  Y  E  K  H  K  V  Y  A  C  E

GTCACCCATCAGGGCCTGAGCTCGCCCGTCACAAAGAGCTTCAACAGGGGAGAGTGT    (SEQ ID NO:17)
661 ---------+---------+---------+---------+---------+--------  720
     V  T  H  Q  G  L  S  S  P  V  T  K  S  F  N  R  G  E  C   (SEQ ID NO:19)
```

Below is a cDNA sequence (SEQ ID NO:18), from which the heavy chain having the amino acid sequence of SEQ ID NO:20 may be expressed.

```
    ATGAACTTCGGGCTCAGCTTGATTTTCCTTGTCCTTGTCTTAAAAGGTGTCCAGTGTGAA
  1 ---------+---------+---------+---------+---------+---------+ 60
     M  N  F  G  L  S  L  I  F  L  V  L  V  L  K  G  V  Q  C  E

GTGCAACTGGTGGAGTCTGGGGGAGGCTTAGTGCAGCCTGGAGGCTCTCTGAGGCTCTCC
 61 ---------+---------+---------+---------+---------+---------+ 120
     V  Q  L  V  E  S  G  G  G  L  V  Q  P  G  G  S  L  R  L  S

TGTGCAGGCTCTGGATTCACTTTCAGTAACTATGGCATGTCTTGGGTTCGCCAGGCTCCT
121 ---------+---------+---------+---------+---------+---------+ 180
     C  A  G  S  G  F  T  F  S  N  Y  G  M  S  W  V  R  Q  A  P

GGAAAGGGACTGGAGTGGGTTGCATCCATTAGGAGTGGTGGTGGTAGAACCTACTATTCA
181 ---------+---------+---------+---------+---------+---------+ 240
     G  K  G  L  E  W  V  A  S  I  R  S  G  G  G  R  T  Y  Y  S

GACAATGTAAAGGGCCGATTCACCATCTCCAGAGAGAATGCCAAGAACAGCCTGTACCTG
241 ---------+---------+---------+---------+---------+---------+ 300
     D  N  V  K  G  R  F  T  I  S  R  E  N  A  K  N  S  L  Y  L

CAAATGAACAGTCTGAGAGCTGAGGACACGGCTGTCTATTATTGTGTCAGATATGATCAC
301 ---------+---------+---------+---------+---------+---------+ 360
     Q  M  N  S  L  R  A  E  D  T  A  V  Y  Y  C  V  R  Y  D  H

TATAGTGGTAGCTCCGACTACTGGGGCCAGGGCACCTTGGTCACAGTCTCCTCAGCCTCC
361 ---------+---------+---------+---------+---------+---------+ 420
     Y  S  G  S  S  D  Y  W  G  Q  G  T  L  V  T  V  S  S  A  S

ACCAAGGGCCCATCGGTCTTCCCCCTGGCACCCTCCTCCAAGAGCACCTCTGGGGGCACA
421 ---------+---------+---------+---------+---------+---------+ 480
     T  K  G  P  S  V  F  P  L  A  P  S  S  K  S  T  S  G  G  T
```

```
                              -continued
      GCGGCCCTGGGCTGCCTGGTCAAGGACTACTTCCCCGAACCGGTGACGGTGTCGTGGAAC
481   ------------------------------------------------------------  540
       A   A   L   G   C   L   V   K   D   Y   F   P   E   P   V   T   V   S   W   N TCAGGCGCCCTGACCAGCGGCGTGCACACCTTCCCGGCTGTCCTACAGTCCTCAGGACTC
541   ------------------------------------------------------------  600
       S   G   A   L   T   S   G   V   H   T   F   P   A   V   L   Q   S   S   G   L TACTCCCTCAGCAGCGTGGTGACCGTGCCCTCCAGCAGCTTGGGCACCCAGACCTACATC
601   ------------------------------------------------------------  660
       Y   S   L   S   S   V   V   T   V   P   S   S   S   L   G   T   Q   T   Y   I TGCAACGTGAATCACAAGCCCAGCAACACCAAGGTGGACAAGAAAGTTGAGCCCAAATCT
661   ------------------------------------------------------------  720
       C   N   V   N   H   K   P   S   N   T   K   V   D   K   K   V   E   P   K   S TGTGACAAAACTCACACATGCCCACCGTGCCCAGCACCTGAACTCCTGGGGGGACCGTCA
721   ------------------------------------------------------------  780
       C   D   K   T   H   T   C   P   P   C   P   A   P   E   L   L   G   G   P   S GTCTTCCTCTTCCCCCCAAAACCCAAGGACACCCTCATGATCTCCCGGACCCCTGAGGTC
781   ------------------------------------------------------------  840
       V   F   L   F   P   P   K   P   K   D   T   L   M   I   S   R   T   P   E   V ACATGCGTGGTGGTGGACGTGAGCCACGAAGACCCTGAGGTCAAGTTCAACTGGTACGTG
841   ------------------------------------------------------------  900
       T   C   V   V   V   D   V   S   H   E   D   P   E   V   K   F   N   W   Y   V GACGGCGTGGAGGTGCATAATGCCAAGACAAAGCCGCGGGAGGAGCAGTACAACAGCACG
901   ------------------------------------------------------------  960
       D   G   V   E   V   H   N   A   K   T   K   P   R   E   E   Q   Y   N   S   T TACCGTGTGGTCAGCGTCCTCACCGTCCTGCACCAGGACTGGCTGAATGGCAAGGAGTAC
961   ------------------------------------------------------------  1020
       Y   R   V   V   S   V   L   T   V   L   H   Q   D   W   L   N   G   K   E   Y AAGTGCAAGGTCTCCAACAAAGCCCTCCCAGCCCCCATCGAGAAAACCATCTCCAAAGCC
1021  ------------------------------------------------------------  1080
       K   C   K   V   S   N   K   A   L   P   A   P   I   E   K   T   I   S   K   A AAAGGGCAGCCCCGAGAACCACAGGTGTACACCCTGCCCCCATCCCGGGATGAGCTGACC
1081  ------------------------------------------------------------  1140
       K   G   Q   P   R   E   P   Q   V   Y   T   L   P   P   S   R   D   E   L   T AAGAACCAGGTCAGCCTGACCTGCCTGGTCAAAGGCTTCTATCCCAGCGACATCGCCGTG
1141  ------------------------------------------------------------  1200
       K   N   Q   V   S   L   T   C   L   V   K   G   F   Y   P   S   D   I   A   V GAGTGGGAGAGCAATGGGCAGCCGGAGAACAACTACAAGACCACGCCTCCCGTGCTGGAC
1201  ------------------------------------------------------------  1260
       E   W   E   S   N   G   Q   P   E   N   N   Y   K   T   T   P   P   V   L   D TCCGACGGCTCCTTCTTCCTCTACAGCAAGCTCACCGTGGACAAGAGCAGGTGGCAGCAG
1261  ------------------------------------------------------------  1320
       S   D   G   S   F   F   L   Y   S   K   L   T   V   D   K   S   R   W   Q   Q GGGAACGTCTTCTCATGCTCCGTGATGCATGAGGCTCTGCACAACCACTACACGCAGAAG
1321  ------------------------------------------------------------  1380
       G   N   V   F   S   C   S   V   M   H   E   A   L   H   N   H   Y   T   Q   K AGCCTCTCCCTGTCTCCGGGTAAA (SEQ ID NO:18)
1381  -----------------------                                       1416
       S   L   S   L   S   P   G   K  (SEQ ID NO:20)
```

The complete sequence of a humanized 3D6 light chain gene with introns (located between MluI and BamHI sites, as in pVk-Hu3D6) is shown below (SEQ ID NO:15). The nucleotide number indicates its position in pVk-Hu3D6. The Vk and Ck exons are translated in single letter code; the dot indicates the translation termination codon. The mature light chain starts at the double-underlined aspartic acid (D). The intron sequence is in italics. The polyA signal is underlined. The expressed light chain corresponds to SEQ ID NO:11 when mature.

```
 619 ACGCGTCCACCATGATGAGTCCTGCCCAGTTCCTGTTTCTGTTAGTGCTCTGGATTCGGGAAACCAACGGTGATGTTGTG
              M  M  S  P  A  Q  F  L  F  L  L  V  L  W  I  R  E  T  N  G  D  V  V

699 ATGACCCAGTCTCCACTCTCCTTGCCTGTTACCCTGGGACAACCAGCCTCCATCTCTTGCAAGTCAAGTCAGAGCCTCTT
      M  T  Q  S  P  L  S  L  P  V  T  L  G  Q  P  A  S  I  S  C  K  S  S  Q  S  L  L

779 AGATAGTGATGGAAAGACATATTTGAATTGGTTGCAACAGCGCCCAGGCCAGTCTCCAAGACGCCTAATCTATCTGGTGT
        D  S  D  G  K  T  Y  L  N  W  L  Q  Q  R  P  G  Q  S  P  R  R  L  I  Y  L  V

859 CTAAACTGGACTCTGGAGTCCCTGACAGGTTCTCTGGCAGTGGATCAGGGACAGATTTTACACTGAAAATCAGCAGAGTC
       S  K  L  D  S  G  V  P  D  R  F  S  G  S  G  S  G  T  D  F  T  L  K  I  S  R  V

939 GAGGCTGAGGATGTGGGAGTTTATTATTGCTGGCAAGGTACACATTTTCCTCGGACGTTCGGTGGAGGCACCAAGGTGGA
       E  A  E  D  V  Y  Y  C  W  Q  G  T  H  F  P  R  T  F  G  G  G  T  K  V  E

1019 AATCAAACGTAAGTGCACTTTCCTTCTAGAATTCTAAACTCTGAGGGGGTCGGATGACGTGGCCAATTCTTTGCCTAAAG
       I  K  R

1099 CATTGAGTTTACTGCAAGGTCAGAAAAGCATGCAAAGCCCTCAGAATGGCTGCAAAGAGCTCCAACAAAACAATTTAGAA

1179 CTTTATTAAGGAATAGGGGGAAGCTAGGAAGAAACTCAAAACATCAAGATTTTAAATACGCTTCTTGGTCTCCTTGCTAT

1259 AATTATCTGGGATAAGCATGCTGTTTTCTGTCTGTCCCTAACATGCCCTGTGATTATCCGCAAACAACACACCCAAGGGC

1339 AGAACTTTGTTACTTAAACACCATCCTGTTTGCTTCTTTCCTCAGGAACTGTGGCTGCACCATCTGTCTTCATCTTCCCG
                                                              T  V  A  A  P  S  V  F  I  F  P

1419 CCATCTGATGAGCAGTTGAAATCTGGAACTGCCTCTGTTGTGTGCCTGCTGAATAACTTCTATCCCAGAGAGGCCAAAGT
       P  S  D  E  Q  L  K  S  G  T  A  S  V  V  C  L  L  N  N  F  Y  P  R  E  A  K  V

1499 ACAGTGGAAGGTGGATAACGCCCTCCAATCGGGTAACTCCCAGGAGAGTGTGCACAGAGCAGGACAGCAAGGACAGCACCT
       Q  W  K  V  D  N  A  L  Q  S  G  N  S  Q  E  S  V  T  E  Q  D  S  K  D  S  T

1579 ACAGCCTCAGCAGCACCCTGACGCTGAGCAAAGCAGACTACGAAGAAACACAAAGTCTACGCCTGCGAAGTCACCCATCAG
       Y  S  L  S  S  T  L  T  L  S  K  A  D  Y  E  K  H  K  V  Y  A  C  E  V  T  H  Q

1659 GGCCTGAGCTCGCCCGTCACAAAGAGCTTCAACAGGGGAGAGTGTTAGAGGGAGAAGTGCCCCCACCTGCTCCTCAGTTC
       G  L  S  S  P  V  T  K  S  F  N  R  G  E  C  ●

1739 CAGCCTGACCCCCTCCCATCCTTTGGCCTCTGACCCTTTTTCCACAGGGGACCTACCCCTATTGCGGTCCTCCAGCTCAT

1819 CTTTCACCTCACCCCCCTCCTCCTCCTTGGCTTTAATTATGCTAATGTTGGAGGAGAATGAATAAATAAA GTGAATCTTT

1899 GCACCTGTGGTTTCTCTCTTTCCTCATTTAATAATTATTATCTGTTGTTTTACCAACTACTCAATTTCTCTTATAAGGGA

1979 CTAAATATGTAGTCATCCTAAGGCGCATAACCATTTATAAAATCATCCTTCATTCTATTTTACCCTATCATCCTCTGCA

2059 AGACAGTCCTCCCTCAAACCCACAAGCCTTCTGTCCTCACAGTCCCCTGGGCCATGGTAGGAGAGACTTGCTTCCTTGTT

2139 TTCCCCTCCTCAGCAAGCCCTCATAGTCCTTTTTAAGGGTGACAGGTCTTACAGTCATATATCCTTTGATTCAATTCCCT

2219 GAGAATCAACCAAAGCAAATTTTTCAAAAGAAGAAACCTGCTATAAAGAGAATCATTCATTGCAACATGATATAAAATAA

2299 CAACACAATAAAAGCAATTAAATAAACAAACAATAGGGAAATGTTTAAGTTCATCATGGTACTTAGACTTAATGGAATGT

2379 CATGCCTTATTTACATTTTTAAACAGGTACTGAGGGACTCCTGTCTGCCAAGGGCCGTATTGAGTACTTTCCACAACCTA

2459 ATTTAATCCACACTATACTGTGAGATTAAAAACATTCATTAAAATGTTGCAAAGGTTCTATAAAGCTGAGAGACAAATAT

2539 ATTCTATAACTCAGCAATCCCACTTCTAGGATC (SEQ ID NO:15)
```

The complete sequence of a humanized 3D6 heavy chain gene with introns (located between MluI and BamHI sites, as in pVg1-Hu3D6) is shown below (SEQ ID NO:16). The nucleotide number indicates its position in pVg1-Hu3D6. The $V_H$ and $C_H$ exons are translated in single letter code; the dot indicates the translation termination codon. The mature heavy chain starts at the double-underlined glutamine (Q). The intron sequences are in italic. The polyA signal is underlined. The expressed heavy chain corresponds to SEQ ID NO:12 when mature.

```
 619 ACGCGTCCACCATGAACTTCGGGCTCAGCTTGATTTTCCTTGTCCTTGTCTTAAAAGGTGTCCAGTGTGAAGTGCAACTG
                    M  N  F  G  L  S  L  I  F  L  V  L  V  L  K  G  V  Q  C  E   V  Q  L

699 GTGGAGTCTGGGGGAGGCTTAGTGCAGCCTGGAGGCTCTCTGAGGCTCTCCTGTGCAGGCTCTGGATTCACTTTCAGTAA
      V  E  S  G  G  G  L  V  Q  P  G  G  S  L  R  L  S  C  A  G  S  G  F  T  F  S  N

779 CTATGGCATGTCTTGGGTTCGCCAGGCTCCTGGAAAGGGACTGGAGTGGGTTGCATCCATTAGGAGTGGTGGTAGAA
        Y  G  M  S  W  V  R  Q  A  P  G  K  G  L  E  W  V  A  S  I  R  S  G  G  R

859 CCTACTATTCAGACAATGTAAAGGGCCGATTCACCATCTCCAGAGAGAATGCCAAGAACAGCCTGTACCTGCAAATGAAC
        T  Y  Y  S  D  N  V  K  G  R  F  T  I  S  R  E  N  A  K  N  S  L  Y  L  Q  M  N

939 AGTCTGAGAGCTGAGGACACGGCTGTCTATTATTGTGTCAGATATGATCACTATAGTGGTAGCTCCGACTACTGGGGCCA
        S  L  R  A  E  D  T  A  V  Y  Y  C  V  R  Y  D  H  Y  S  G  S  S  D  Y  W  G  Q

1019 GGGCACCTTGGTCACAGTCTCCTCAGGTGAGTCCTCACAACCTCTAGAGCTTTCTGGGGCAGGCCAGGCCTGACCTTGGC
        G  T  L  V  T  V  S  S

1099 TTTGGGGCAGGGAGGGGGCTAAGGTGAGGCAGGTGGCGCCAGCCAGGTGCACACCCAATGCCCATGAGCCCAGACACTGG

1179 ACGCTGAACCTCGCGGACAGTTAAGAACCCAGGGGCCTCTGCGCCCTGGGCCCAGCTCTGTCCCACACCGCGGTCACATG

1259 GCACCACCTCTCTTGCAGCCTCCACCAAGGGCCCATCGGTCTTCCCCCTGGCACCCTCCTCCAAGAGCACCTCTGGGGGC
                         A  S  T  K  G  P  S  V  F  P  L  A  P  S  S  K  S  T  S  G  G

1339 ACAGCGGCCCTGGGCTGCCTGGTCAAGGACTACTTCCCCGAACCGGTGACGGTGTCGTGGAACTCAGGCGCCCTGACCAG
      T  A  A  L  G  C  L  V  K  D  Y  F  P  E  P  V  T  V  S  W  N  S  G  A  L  T  S

1419 CGGCGTGCACACCTTCCCGGCTGTCCTACAGTCCTCAGGACTCTACTCCCTCAGCAGCGTGGTGACCGTGCCCTCCAGCA
        G  V  H  T  F  P  A  V  L  Q  S  S  G  L  Y  S  L  S  S  V  V  T  V  P  S  S

1499 GCTTGGGCACCCAGACCTACATCTGCAACGTGAATCACAAGCCCAGCAACACCAAGGTGGACAAGAAAGTTGGTGAGAGG
        S  L  G  T  Q  T  Y  I  C  N  V  N  H  K  P  S  N  T  K  V  D  K  K  V

1579 CCAGCACAGGGAGGGAGGGTGTCTGCTGGAAGCCAGGCTCAGCGCTCCTGCCTGGACGCATCCCGGCTATGCAGCCCCAG

1659 TCCAGGGCAGCAAGGCAGGCCCCGTCTGCCTCTTCACCCGGAGGCCTCTGCCCGCCCCACTCATGCTCAGGGAGAGGGTC

1739 TTCTGGCTTTTTCCCCAGGCTCTGGGCAGGCACAGGCTAGGTGCCCCTAACCCAGGCCCTGCACACAAAGGGGCAGGTGC

1819 TGGGCTCAGACCTGCCAAGAGCCATATCCGGGAGGACCCTGCCCCTGACCTAAGCCCACCCCAAAGGCCAAACTCTCCAC

1899 TCCCTCAGCTCGGACACCTTCTCTCCTCCCAGATTCCAGTAACTCCCAATCTTCTCTCTGCAGAGCCCAAATCTTGTGAC
                                                                      E  P  K  S  C  D

1979 AAAACTCACACATGCCCACCGTGCCCAGGTAAGCCAGCCCAGGCCTCGCCCTCCAGCTCAAGGCGGGACAGGTGCCCTAG
      K  T  H  T  C  P  P  C  P

2059 AGTAGCCTGCATCCAGGGACAGGCCCCAGCCGGGTGCTGACACGTCCACCTCCATCTCTTCCTCAGCACCTGAACTCCTG
        A  P  E  L  L

2139 GGGGGACCGTCAGTCTTCCTCTTCCCCCCAAAACCCAAGGACACCCTCATGATCTCCCGGACCCCTGAGGTCACATGCGT
        G  G  P  S  V  F  L  F  P  P  K  P  K  D  T  L  M  I  S  R  T  P  E  V  T  C  V

2219 GGTGGTGGACGTGAGCCACGAAGACCCTGAGGTCAAGTTCAACTGGTACGTGGACGGCGTGGAGGTGCATAATGCCAAGA
        V  V  D  V  S  H  E  D  P  E  V  K  F  N  W  Y  V  D  G  V  E  V  H  N  A  K

2299 CAAAGCCGCGGGAGGAGCAGTACAACAGCACGTACCGTGTGGTCAGCGTCCTCACCGTCCTGCACCAGGACTGGCTGAAT
        T  K  P  R  E  E  Q  Y  N  S  T  Y  R  V  V  S  V  L  T  V  L  H  Q  D  W  L  N

2379 GGCAAGGAGTACAAGTGCAAGGTCTCCAACAAAGCCCTCCCAGCCCCCATCGAGAAAACCATCTCCAAAGCCAAAGGTGG
        G  K  E  Y  K  C  K  V  S  N  K  A  L  P  A  P  I  E  K  T  I  S  K  A  K

2459 GACCCGTGGGGTGCGAGGGCCACATGGACAGAGGCCGGCTCGGCCCACCCTCTGCCCTGAGAGTGACCGCTGTTACCAACC
```

-continued
```
2539 TCTGTCCCTACAGGGCAGCCCCTGAGAACCACAGGTGTACACCCTGCCCCCATCCCGGGATGAGCTGACCAAGAACCAGGT
        G   Q   P   R   E   P   Q   V   Y   T   L   P   P   S   R   D   E   L   T   K   N   Q   V 2619 CAGCCTGACCTGCCTGGTCAAAGGCTTCTATCCCAGCGACATCGCCGTGGAGTGGGAGAGCAAATGGGCAGCCGGAGAACA
       S   L   T   C   L   V   K   G   F   Y   P   S   D   I   A   V   E   W   E   S   N   G   Q   P   E   N 2699 ACTACAAGACCACGCCTCCCGTGCTGGACTCCGACGGCTCCTTCTTCCTCTACAGCAAGCTCACCGTGGACAAGAGCAGG
       N   Y   K   T   T   P   P   V   L   D   S   D   G   S   F   F   L   Y   S   K   L   T   V   D   K   S   R 2779 TGGCAGCAGGGGAACGTCTTCTCATGCTCCGTGATGCATGAGGCTCTGCACAACCACTACACGCAGAAGAGCCTCTCCCT
       W   Q   Q   G   N   V   F   S   C   S   V   M   H   E   A   L   H   N   H   Y   T   Q   K   S   L   S   L 2859 GTCTCCGGGTAAATGAGTGCGACGGCCGGCAAGCCCCGCTCCCGGGCTCTCGCGGTCGCACGAGGATGCTTGGCACGT
       S   P   G   K   •

2939 ACCCCCTGTACATACTTCCCGGGCGCCCAGCATGGAAATAAA GCACCCAGCGCTGCCCTGGGCCCCTGCGAGACTGTGAT

3019 GGTTCTTTCCACGGGTCAGGCCGAGTCTGAGGCCTGAGTGGCATGAGGGAGGCAGAGCGGGTCCCACTGTCCCCACACTG

3099 GCCCAGGCTGTGCAGGTGTGCCTGGGCCGCCTAGGGTGGGGCTCAGCCAGGGGCTGCCCTCGGCAGGGTGGGGGATTTGC

3179 CAGCGTGGCCCTCCCTCCAGCAGCACCTGCCCTGGGCTGGGCCACGGGAAGCCCTAGGAGCCCCTGGGGACAGACACACA

3259 GCCCCTGCCTCTGTAGGAGACTGTCCTGTTCTGTGAGCGCCCTGTCCTCCGACCTCCATGCCCACTCGGGGGCATGCCTA

3339 GTCCATGTGCGTAGGGACAGGCCCTCCCTCACCCATCTACCCCCACGGCACTAACCCCTGGCTGCCCTGCCCAGCCTCGC

3419 ACCCGCATGGGGACACAACCGACTCCGGGGACATGCACTCTCGGGCCCTGTGGAGGGACTGGTGCAGATGCCCACACACA

3499 CACTCAGCCCAGACCCGTTCAACAAACCCCGCACTGAGGTTGGCCGGCCACACGGCCACCACACACACGTGCACGCCT

3579 CACACACGGAGCCTCACCCGGGCGAACTGCACAGCACCCAGACCAGAGCAAGGTCCTCGCACACGTGAACACTCCTCGGA

3659 CACAGGCCCCACGAGCCCCACGCGGCACCTCAAGGCCCACGAGCCTCTCGGCAGCTTCTCCACATGCTGACCTGCTCAG

3739 ACAAACCCAGCCCTCCTCTCACAAGGGTGCCCCTGCAGCCGCCACACACACAGGGGATCACACACCACGTCACGTCCC

3819 TGGCCCTGGCCCACTTCCCAGTGCCGCCCTTCCCTGCAGGATCC (SEQ ID NO:16)
```

Human constant region DNA sequences can be isolated in accordance with well known procedures from a variety of human cells, but preferably from immortalized B-cells. Suitable source cells for the polynucleotide sequences and host cells for immunoglobulin expression and secretion can be obtained from a number of sources well-known in the art.

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors using site-directed mutagenesis, such as after CH1 to produce Fab fragments or after the hinge region to produce F(ab')$_2$ fragments. Single chain antibodies may be produced by joining VL and VH with a DNA linker.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences.

*E. coli* is a prokaryotic host useful particularly for cloning the polynucleotides of the present invention. Other microbial hosts suitable for use include bacilli, such as *Bacillus subtilus*, and other enterobacteriaceae, such as *Salmonella*, *Serratia*, and various *Pseudomonas* species. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention. Eukaryotic cells are actually preferred, because a number of suitable host cell lines capable of secreting intact immunoglobulins have been developed in the art, and include the CHO cell lines, various COS cell lines, Syrian Hamster Ovary cell lines, HeLa cells, preferably myeloma cell lines, transformed B-cells, human embryonic kidney cell lines, or hybridomas. Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Once expressed, the antibodies can be purified according to standard procedures, including ammonium sulfate precipitation, ion exchange, affinity, reverse phase, hydrophobic interaction column chromatography, gel electrophoresis, and the like. Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically or prophylactically, as directed herein.

The antibodies (including immunologically reactive fragments) are administered to a subject at risk for or exhibiting Aβ-related symptoms or pathology such as clinical or pre-clinical Alzheimer's disease, Down's syndrome, or clinical or pre-clinical amyloid angiopathy, using standard administration techniques, preferably peripherally (i.e. not by administration into the central nervous system) by intravenous, intraperitoneal, subcutaneous, pulmonary, transdermal, intramuscular, intranasal, buccal, sublingual, or suppository administration. Although the antibodies may be administered directly into the ventricular system, spinal fluid, or brain parenchyma, and techniques for addressing these locations are well known in the art, it is not necessary to utilize these more difficult procedures. The antibodies of the invention are effective when administered by the more simple techniques that rely on the peripheral circulation system. The advantages of the present invention include the ability of the antibody to exert its beneficial effects even though not provided directly to the central nervous system itself. Indeed, it has been demonstrated that the amount of antibody that crosses the bloodbrain barrier is ≦0.1% of plasma levels.

The pharmaceutical compositions for administration are designed to be appropriate for the selected mode of administration, and pharmaceutically acceptable excipients such as, buffers, surfactants, preservatives, solubilizing agents, isotonicity agents, stabilizing agents and the like are used as appropriate. *Remington's Pharmaceutical Sciences*, Mack Publishing Co., Easton Pa., latest edition, incorporated herein by reference, provides a compendium of formulation techniques as are generally known to practitioners.

The concentration of the humanized antibody in formulations may range from as low as about 0.1% to as much as 15 or 20% by weight and will be selected primarily based on fluid volumes, viscosities, and so forth, in accordance with the particular mode of administration selected. Thus, a pharmaceutical composition for injection could be made up to contain in 1 mL of phosphate buffered saline from 1 to 100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration. Therapeutic agents of the invention can be frozen or lyophilized for storage and reconstituted in a suitable sterile carrier prior to use. Lyophilization and reconstitution can lead to varying degrees of antibody activity loss (e.g. with conventional immune globulins, IgM antibodies tend to have greater activity loss than IgG antibodies). Dosages may have to be adjusted to compensate. The pH of the formulation will be selected to balance antibody stability (chemical and physical) and comfort to the patient when administered. Generally, pH between 4 and 8 is tolerated.

Although the foregoing methods appear the most convenient and most appropriate for administration of proteins such as humanized antibodies, by suitable adaptation, other techniques for administration, such as transdermal administration and oral administration may be employed provided proper formulation is designed. In addition, it may be desirable to employ controlled release formulations using biodegradable films and matrices, or osmotic mini-pumps, or delivery systems based on dextran beads, alginate, or collagen. In summary, formulations are available for administering the antibodies of the invention and are well-known in the art and may be chosen from a variety of options. Typical dosage levels can be optimized using standard clinical techniques and will be dependent on the mode of administration and the condition of the patient.

The following examples are intended to illustrate but not to limit the invention. Because the examples here describe experiments conducted in murine systems, the use of murine monoclonal antibodies is satisfactory. However, in the treatment methods of the invention intended for human use, humanized forms of the antibodies with the immunospecificity corresponding to that of antibody 3D6 are preferred.

EXAMPLE 1

Synthesis of Humanized Antibody 3D6

Cells and antibodies. Mouse myeloma cell line Sp2/0 was obtained from ATCC (Manassas, Va.) and maintained in DME medium containing 10% FBS (Cat # SH30071.03, HyClone, Logan, Utah) in a 37° C. $CO_2$ incubator. Mouse 3D6 hybridoma cells were first grown in RPMI-1640 medium containing 10% FBS (HyClone), 10 mM HEPES, 2 mM glutamine, 0.1 mM non-essential amino acids, 1 mM sodium pyruvate, 25 µg/ml gentamicin, and then expanded in serum-free media (Hybridoma SFM, Cat # 12045-076, Life Technologies, Rockville, Md.) containing 2% low Ig FBS (Cat # 30151.03, HyClone) to a 1.5 liter volume in roller bottles. Mouse monoclonal antibody 3D6 (Mu3D6) was purified from the culture supernatant by affinity chromatography using a protein-G Sepharose column. Biotinylated Mu3D6 was prepared using EZ-Link Sulfo-NHS-LC-LC-Biotin (Cat # 21338ZZ, Pierce, Rockford, Ill.).

Cloning of variable region cDNAs. Total RNA was extracted from approximately $10^7$ hybridoma cells using TRIzol reagent (Cat. # 15596-026 Life Technologies) and poly(A)+ RNA was isolated with the PolyATract mRNA Isolation System (Cat. # Z5310, Promega, Madison, Wis.) according to the suppliers' protocols. Double-stranded cDNA was synthesized using the SMART™RACE cDNA Amplification Kit (Cat. # K1811-1, Clontech, Palo Alto, Calif.) following the supplier's protocol. The variable region cDNAs for the light and heavy chains were amplified by polymerase chain reaction (PCR) using 3' primers that anneal respectively to the mouse kappa and gamma chain constant regions, and a 5' universal primer provided in the SMART™RACE cDNA Amplification Kit. For VL PCR, the 3' primer has the sequence:

[SEQ ID NO: 13]
5'-TATAGAGCTCAAGCTTGGATGGTGGGAAGATGGATACAGTTGGTGC-3' with residues 17-46 hybridizing to the mouse Ck region. For VH PCR, the 3' primers have the degenerate sequences:

```
                                         [SEQ ID NO:14]
                        A        G    T
5'-TATAGAGCTCAAGCTTCCAGTGGATAGACCGATGGGGCTGTCGTT
                                 T
TTGGC-3'
``` with residues 17-50 hybridizing to mouse gamma chain CH1. The VL and VH cDNAs were subcloned into pCR4Blunt-TOPO vector (Cat. # 45-0031, Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructionas. The sequencing reactions were analyzed on a Model 377 DNA Sequencer (Applied Biosystems).

Construction of humanized 3D6 (Hu3D6) variable regions. Humanization of the mouse antibody V regions was carried out as outlined by Queen et al., (1989), op. cit. The human V region framework used as acceptor for Mu3D6 CDRs was chosen based on sequence homology. The computer programs ABMOD and ENCAD [Levitt, M., J. Mol. Biol. 168:595-620 (1983)] were used to construct a molecular model of the variable regions. Amino acids in the humanized V regions that were predicted to have contact with CDRs were substituted with the corresponding residues of Mu3D6. This was done at residues 49, 73, and 98 in the heavy chain and at residue 41 in the light chain. The amino acids in the humanized V region that were found to be rare in the same V-region subgroup were changed to the consensus amino acids to eliminate potential immunogenicity. This was done at residues 6 and 91 in the heavy chain.

The light and heavy chain variable region genes were constructed and amplified using eight overlapping synthetic oligonucleotides ranging in length from approximately 65 to 80 bases [He, X. Y., et al., J. Immunol. 160: 029-1035 (1998)]. The oligonucleotides were annealed pairwise and extended with the Klenow fragment of DNA polymerase I, yielding four double-stranded fragments. The resulting fragments were denatured, annealed pairwise, and extended with Klenow, yielding two fragments. These fragments were denatured, annealed pairwise, and extended once again, yielding a full-length gene. The resulting product was amplified by PCR using the Expand High Fidelity PCR System (Cat. # 1 732 650, Roche Molecular Biochemicals, Indianapolis, Ind.). The PCR-amplified fragments were gel-purified and cloned into pCR4Blunt-TOPO vector. After sequence confirmation, the VL and VH genes were digested with MluI and XbaI, gel-purified, and subcloned respectively into vectors for expression of light and heavy chains to make pVk-Hu3D6 and pVg1-Hu3D6 [Co, M. S., et al., J. Immunol. 148:1149-1154 (1992)]. The mature humanized 3D6 antibody expressed from these plasmids has the light chain of SEQ ID NO:11 and the heavy chain of SEQ ID NO:12.

Stable transfection. Stable transfection into mouse myeloma cell line Sp2/0 was accomplished by electroporation using a Gene Pulser apparatus (BioRad, Hercules, Calif.) at 360 V and 25 µF as described (Co, et al., 1992, op. cit.). Before transfection, pVk-Hu3D6 and pVg1-Hu3D6 plasmid DNAs were linearized using FspI and BstZ171, respectively. Approximately $10^7$ Sp2/0 cells were transfected with 20 µg of pVk-Hu3D6 and 40 µg of pVg1-Hu3D6. The transfected cells were suspended in DME medium containing 10% FBS and plated into several 96-well plates. After 48 hr, selection media (DME medium containing 10% FBS, HT media supplement, 0.3 mg/ml xanthine and 1 µg/ml mycophenolic acid) was applied. Approximately 10 days after the initiation of the selection, culture supernatants were assayed for antibody production by ELISA as shown below. High yielding clones were expanded in DME medium containing 10% FBS and further analyzed for antibody expression. Selected clones were then adapted to growth in Hybridoma SFM.

Measurement of antibody expression by ELISA. Wells of a 96-well ELISA plate (Nunc-Immuno plate, Cat # 439454, NalgeNunc, Naperville, Ill.) were coated with 100 µl of 1 µg/ml goat anti-human IgG, Fc γ fragment specific, polyclonal antibodies (Cat # 109-005-098, Jackson ImmunoResearch, West Grove, Pa.) in 0.2 M sodium carbonate-bicarbonate buffer (pH 9.4) overnight at 4° C. After washing with Washing Buffer (PBS containing 0.1% Tween 20), wells were blocked with 400 µl of Superblock Blocking Buffer (Cat # 37535, Pierce) for 30 min and then washed with Washing Buffer. Samples containing Hu3D6 were appropriately diluted in ELISA Buffer (PBS containing 1% BSA and 0.1% Tween 20) and applied to ELISA plates (100 µl per well). As a standard, humanized anti-CD33 IgG1 monoclonal antibody HuM195 (Co, et al., 1992, op. cit.) was used. The ELISA plate was incubated for 2 hr at room temperature and the wells were washed with Washing Buffer. Then, 100 µl of 1/1,000-diluted HRP-conjugated goat anti-human kappa polyclonal antibodies (Cat # 1050-05, Southern Biotechnology, Birmingham, Ala.) in ELISA Buffer was applied to each well. After incubating for 1 hr at room temperature and washing with Washing Buffer, 100 µl of ABTS substrate (Cat #s 507602 and 506502, Kirkegaard and Perry Laboratories, Gaithersburg, Md.) was added to each well. Color development was stopped by adding 100 µl of 2% oxalic acid per well. Absorbance was read at 415 nm using an OPTImax microplate reader (Molecular Devices, Menlo Park, Calif.).

Purification of Hu3D6. One of the high Hu3D6-expressing Sp2/0 stable transfectants (clone #40) was adapted to growth in Hybridoma SFM and expanded to 2 liters in roller bottles. Spent culture supernatant was harvested when cell viability reached 10% or below and loaded onto a protein-A Sepharose column. The column was washed with PBS before the antibody was eluted with 0.1 M glycine-HCl (pH 2.5), 0.1 M NaCl. The eluted protein was dialyzed against 3 changes of 2 liters of PBS and filtered through a 0.2 µm filter prior to storage at 4° C. Antibody concentration was determined by measuring absorbance at 280 nm (1 mg/ml=1.4 $A_{280}$). SDS-PAGE in Tris-glycine buffer was performed according to standard procedures on a 4-20% gradient gel (Cat # EC6025, Novex, San Diego, Calif.). Purified humanized 3D6 antibody is reduced and run on an SDS-PAGE gel.

The whole antibody shows two bands of approximate molecular weights 25 kDa and 50 kDa. These results are consistent with the molecular weights of the light chain and heavy chain, or with the molecular weight of the chain(s) comprising a fragment, calculated from their amino acid compositions.

EXAMPLE 2

It Vitro Binding Properties of Humanized 3D6 Antibody

The binding efficacy of humanized 3D6 antibody, synthesized and purified as described above, was compared with the mouse 3D6 antibody using biotinylated mouse 3D6 antibody in a comparative ELISA. Wells of a 96-well ELISA plate (Nunc-Immuno plate, Cat # 439454, NalgeNunc) were coated with 100 µl of β-amyloid peptide (1-42) in 0.2 M sodium carbonate/bicarbonate buffer (pH 9.4) (0.3 µg/mL) overnight at 4° C.

After washing the wells with phosphate buffered saline (PBS) containing 0.1% Tween 20 (Washing Buffer) using an ELISA plate washer, the wells were blocked by adding 300 µL of SuperBlock reagent (Pierce) per well. After 30 minutes of blocking, the wells were washed with Washing Buffer and excess liquid was removed.

A mixture of biotinylated Mu3D6 (0.2 µg/ml final concentration) and competitor antibody (Mu3D6 or Hu3D6; starting at 300 µg/ml final concentration and serial 3-fold dilutions) in ELISA Buffer were added in triplicate in a final volume of 100 µl per well. As a no-competitor control, 100 µl of 0.2 µg/ml biotinylated Mu3D6 was added. As a background control, 100 µl of ELISA Buffer was added. The ELISA plate was incubated at room temperature for 90 min. After washing the wells with Washing Buffer, 100 µl of 1 µg/ml HRP-conjugated streptavidin (Cat # 21124, Pierce) was added to each well. The plate was incubated at room temperature for 30 min and washed with Washing Buffer. For color development, 100 µl/well of ABTS Peroxidase Substrate (Kirkegaard & Perry Laboratories) was added. Color development was stopped by adding 100 µl/well of 2% oxalic acid. Absorbance was read at 415 nm. The absorbances were plotted against the log of the competitor concentration, curves were fit to the data points (using Prism) and the IC50 was determined for each antibody using methods well-known in the art.

The mean IC50 for mouse 3D6 was 2.7 µg/mL (three separate experiments, standard deviation=0.6 µg/mL) and for humanized 3D6 was 3.3 µg/mL (three separate experiments, standard deviation=0.8 µg/mL). A second set of three experiments was carried out, essentially as described above, and the mean IC50 for mouse 3D6 was determined to be 3.97 µg/mL (SD=0.15 µg/mL) and for humanized 3D6, the IC50 was determined to be 3.97 µg/mL (SD=0.20 µg/mL). On the basis of these results, we conclude that humanized 3D6 has binding properties that are very similar to those of the mouse antibody 3D6. Therefore, we expect that humanized 3D6 has very similar in vitro and in vivo activities compared with mouse 3D6 and will exhibit in humans the same effects demonstrated with mouse 3D6 in mice.

EXAMPLE 3

In Vitro Binding Properties of Mouse and Humanized Antibodies 3D6

Antibody affinity (KD=Kd/Ka) was determined using a BIAcore biosensor 2000 and data analyzed with BIAevaluation (v. 3.1) software. A capture antibody (rabbit anti-mouse or anti-human IgG) was coupled via free amine groups to carboxyl groups on flow cell 2 of a biosensor chip (CM5) using N-ethyl-N-dimethylaminopropyl carbodiimide and N-hydroxysuccinimide (EDC/NHS). A non-specific rabbit IgG was coupled to flow cell 1 as a background control. Monoclonal antibodies were captured to yield 300 resonance units (RU). Amyloid-beta 1-40 or 1-42 (Biosource International, Inc.) was then flowed over the chip at decreasing concentrations (1000 to 0.1 times KD). To regenerate the chip, bound anti-Aβ antibody was eluted from the chip using a wash with glycine-HCl (pH 2). A control injection containing no amyloid-beta served as a control for baseline subtraction. Sensorgrams demonstrating association and dissociation phases were analyzed to determine Kd and Ka. The affinity (KD) of mouse antibody 3D6 for Aβ 1-42 was determined to be 2.4 nM, and the affinity of humanized 3D6, prepared essentially as described in Example 1, was determined to be 2.3 nM.

EXAMPLE 4

Epitope Mapping of Mouse and Humanized 3D6

The BIAcore is an automated biosensor system for measuring molecular interactions [Karlsson R., et al. *J Immunol. Methods* 145:229-240 (1991)]. The advantage of the BIAcore over other binding assays is that binding of the antigen can be measured without having to label or immobilize the antigen (i.e. the antigen maintains a more native conformation). The BIAcore methodology was used to assess the binding of various amyloid-beta peptide fragments to either mouse 3D6 or humanized 3D6 (prepared substantially as described in Example 1). All dilutions were made with HEPES buffered saline containing Tween 20. A single concentration of a variety of fragments of human Aβ or mouse Aβ 1-40 (BioSource International) was used. Human amyloid beta fragments 1-10 and 1-20 bound to mouse 3D6 and to humanized 3D6, while human Aβ fragments 10-20 and 16-25 did not bind to either antibody. Neither mouse 3D6 nor humanized 3D6 bound mouse Aβ1-40. Using this methodology, the binding epitope for both mouse and humanized 3D6 appears to be between amino acids 1 and 10 of human Aβ.

EXAMPLE 5

Effects of Administration of 3D6

Unless otherwise stated, all studies used $APP^{V717F}$ (PDAPP) transgenic mice, and all injections were i.p. In general, a control group of mice received injections of saline.

Six weeks of weekly injection of 360 µg of 3D6 in old, hemizygous mice (24 month) lowered hippocampal insoluble $A\beta_{total}$ by 10% and Aβ1-42 by 1% (N.S., not statistically significant) in 9 animals per control group and 10 animals per antibody group. In the cortex, mean insoluble $A\beta_{total}$ was lower by 33% and Aβ 1-42 by 47% (p<0.05), while insoluble Aβ 1-40 increased by 100%.

In hemizygous, 4 month old mice, administration of 360 μg of 3D6 per animal: 1) raised average plasma Aβ1-40 and Aβ1-42 levels approximately 6-fold and 9-fold, respectively, by 24 hours after administration; and 2) had no significant effect on soluble Aβ 1-40 in the cortex after 24 hours compared with saline control (5 animals per group). In another study with hemizygous, 3 month old mice, administration of 360 μg of 3D6 per animal raised average plasma Aβ1-42 levels approximately 8-fold by 24 hours after administration.

Administration of 360 μg of 3D6 per animal (5 animals per group, saline control): raised average plasma Aβ 1-40 and Aβ 1-42 levels approximately 92-fold and 32-fold, respectively, by 24 hours after administration ($p<0.05$); lowered cortical insoluble Aβ 1-40 by 42% ($p<0.05$) and Aβ 1-42 by 27% (N.S.), but increased Aβ$_{total}$ by 35% (N.S.); had no consistent or significant effect on soluble or insoluble Aβ 1-40, Aβ 1-42, or Aβ$_{total}$ in the hippocampus after 24 hours; in the cerebellum, increased soluble Aβ 1-42 by 80% ($p<0.001$) and Aβ$_{total}$ by 68% (N.S.), but lowered soluble Aβ 1-40 by 0.6% (N.S.); and in the cerebellum, lowered insoluble Aβ 1-40, Aβ 1-42, and Aβ$_{total}$ by 35% ($p<0.01$), 21% (N.S.), and 12% (N.S.), respectively.

In young mice, administration of 360 μg of 3D6 per animal (5 per group): 1) raised average plasma Aβ 1-42 levels approximately 3-fold by 24 hours after administration; and 2) in the cortex, lowered insoluble Aβ 1-40 about 10% and increased insoluble Aβ 1-42 about 12%.

Studies were conducted to assess the effects of 3D6 on formation of stable Aβ:antibody complexes in biological fluids, plasma Aβ concentrations acutely after administration, cognitive performance after acute or chronic administration, and guanidine-extracted and immunohistochemically-detected Aβ deposition (in brain) after chronic administration.

Mice (3 months of age) were injected with 360 μg of 3D6. Twenty-four hours following antibody administration plasma was collected and proteins were resolved by gel electrophoresis under native (non-denaturing conditions) on a polyacrylamide gel. Following transfer of size fractionated proteins to a solid matrix, complexes were immunodetected with biotinylated antibody and visualized with enhanced chemiluminescence. Unlike certain other anti-Aβ antibodies, no complex was detected with 3D6.

Young (2-3 months of age) mice were injected with 3D6. At various times following antibody administration, plasma was collected and various Aβ species were determined by a sandwich ELISA. Administration of 3D6 resulted in a dose- and time-dependent increase in plasma Aβ levels. Aβ$_{1-40}$ levels increased to a greater degree than Aβ$_{1-42}$ levels following 3D6 administration. In an additional study, young APP$^{V717F}$ tg mice were treated with 360 μg 3D6 and plasma AD levels were measured at 0.5, 3, 6, and 24 h following injection. 3D6 increased plasma Aβ levels in a time-dependent manner.

Extensive behavioral characterization of APP$^{V717F}$tg mice has been performed using several memory paradigms (bar-press, 8 arm-radial maze, object recognition). These mice are impaired in several learning and memory tasks, and deficits in the object recognition (OR) task worsen with age. Therefore, the OR task has been used to assess learning and memory in APP$^{V717F}$tg mice. Performance in the OR task is preferentially dependent on the integrity of the medial temporal lobe (perirhinal and entorhinal cortices). The OR test relies on the spontaneous tendency of rodents to preferentially explore a novel versus familiar object.

On the first day of testing, mice were allowed to habituate to an open field chamber for 50 minutes. The following day, mice were placed back into the open field for two 10-min trials. During trial one, mice were allowed to explore the open field in the presence of an object (e.g., marble or die). Following a 3-hr inter-trial delay, mice were placed back into the open field with the familiar object (the same object explored previously during trial 1) as well as a novel object. The time spent exploring the novel object as well as the familiar object was recorded and a recognition index (the ratio of time spent exploring the novel object×100/total time spent exploring both objects) was calculated for each mouse. Administration of 360 μg of 3D6 per animal 24 hours prior to the habituation session in 11-12 month old APP$^{V717F}$tg mice improved OR performance in 2 of 8 mice tested ($p<0.05$).

Homozygous tg mice (5-6 months old) were administered weekly injections of PBS and 72, 217, and 360 μg of a non-specific IgG or 3D6 (n=19-30) for 5 months. At necropsy, the brains were removed and processed for Aβ ELISA assays and immunohistochemical analysis of parenchymal Aβ burden. Cortical and hippocampal tissues were homogenized in PBS. PBS-insoluble Aβ was subsequently extracted from the pellets by homogenization in 5.5 M guanidine-HCl. Following homogenization, the samples were nutated for at least 24 h prior to centrifugation and collection of the guanidine extract. PBS-soluble and guanidine-extracted tissue preparations were stored at −80° C. for subsequent Aβ ELISA determinations. Immunohistochemical (IHC) analysis of parenchymal Aβ burden was carried out as follows. Eight (8) μm paraffin embedded paraformaldehyde fixed tissues were labeled with rabbit polyclonal anti-Aβ antibody (against Aβ 15-30) and followed by anti-rabbit IgG fluorescent detection. Eight (8) sections of brain (7 IHC, 1 control) were examined from each animal. Treatment with 3D6 (360 μg) markedly and significantly reduced cortical guanidine-extracted Aβ1-42 (by ELISA) and cortical and hippocampal Aβ plaque burden (by IHC), but no effect was observed at lower 3D6 doses. Although no effect on guanidine extracted Aβ1-42 was observed at lower 3D6 doses, these doses significantly reduced cortical and hippocampal Aβ plaque burden (by IHC).

Radiolabeled (15 μCi/mouse, 0.5 mg/mouse) 3D6 was administered to ICR (non-transgenic) mice in order to evaluate kinetics and brain distribution of the antibody after administration by the intravenous route. Plasma kinetics for 3D6 immunoreactivity demonstrated a half-life of elimination of approximately 5 days. TCA-precipitable radioactivity was greater than 95% of the total plasma counts throughout the study, and declined in the plasma compartment with a terminal half-life of 3-4 days. The observation that plasma radioactivity remained predominantly TCA-precipitable throughout the study suggests that the radiolabeled antibody was not significantly proteolytically degraded, nor was the 125-I label cleaved from the antibody over the time course studied. The shapes of the concentration versus time profiles as measured by ELISA and radioactivity were generally similar, with some differences in the terminal phases. There was no apparent accumulation of radiolabel in any tissue, including brain. Distribution of radioactivity to the brain was minimal. The amount of radioactivity associated with the brain samples in this experiment cannot be clearly distinguished from contamination by the blood compartment during tissue processing or from antibody associated with endothelial cells in the brain vasculature.

Nine month old, hemizygous mice received PBS, a non-specific IgG, or 3D6 (500 μg/week) by weekly injection for six months (PBS, 11 animals; IgG, 13 animials; and 3D6, 14 animals). Weak, but statistically significant, Aβ lowering in the cortex (compared to IgG) and hippocampus (compared to IgG or combined PBS/IgG controls) was seen. Immunohistochemical (IHC) analysis showed strong reductions in Aβ plaque burden in the cortex and hippocampus of 3D6-treated mice (94% and 85% reductions, respectively, versus PBS control; p<0.05, and p<0.01, respectively).

EXAMPLE 6

Administration of Humanized 3D6

A preparation of an anti-Aβ antibody comprising a light chain having the amino acid sequence of SEQ ID NO:11 and a heavy chain having the amino acid sequence of SEQ ID NO:12 (a humanized 3D6) was administered as a single intravenous bolus injection to two groups of 12 male marmosets at doses of 1 and 10 mg/kg. Concentrations of immunoreactive anti-Aβ antibody declined with a half-life of elimination of approximately 4 days. $C_{max}$ and AUC parameters increased proportionally between the 1 and 10 mg/kg dose levels. The administration of humanized 3D6 to marmosets resulted in 18 or 29-fold increase in plasma $Aβ_{1-40}$ immunoreactivity after 8 hours, compared with pre-dose concentrations in the 1 and 10 mg/kg dose groups, respectively. Animals at both dose levels had concentrations of $Aβ_{1-40}$ immunoreactivity above baseline levels up to 2 weeks after antibody administration. Kinetic analysis of concentrations of $Aβ_{1-40}$ immunoreactivity showed that the half-life of elimination of $Aβ_{1-40}$ immunoreactivity was comparable to that of the antibody (~4 days). The pharmacokinetics of humanized 3D6 were also evaluated in male cynomolgus monkeys after a single intravenous administration of 1 mg/kg. Analysis of immunoreactivity showed that humanized 3D6 was eliminated from the plasma with a half-life of approximately 11-12 days.

We claim:

1. An antibody comprising a light chain variable region comprising SEQ ID NO:9 and a heavy chain variable region comprising SEQ ID NO:10.

2. A polynucleotide compound, comprising a sequence coding for either SEQ ID NO:9 or SEQ ID NO:10 of the antibody of claim 1.

3. A cell culture wherein the cultured cells express the antibody of claim 1.

4. A pharmaceutical composition, comprising the antibody of claim 1 and a pharmaceutically acceptable excipient.

5. A method for increasing plasma Aβ levels or reducing brain Aβ plaque burden in a human subject, comprising administering to the human subject an effective amount of the antibody of claim 1.

6. An antibody comprising a light chain variable region comprising SEQ ID NO:11 and a heavy chain variable region comprising SEQ ID NO:12.

7. A polynucleotide compound, comprising a sequence coding for either SEQ ID NO:11 or SEQ ID NO:12 of the antibody of claim 6.

8. A cell culture wherein the cultured cells express the antibody of claim 6.

9. A pharmaceutical composition, comprising the antibody of claim 6 and a pharmaceutically acceptable excipient.

10. A method for increasing plasma Aβ levels or reducing brain Aβ plaque burden in a human subject, comprising administering to the human subject an effective amount of the antibody of claim 6.

11. An antibody fragment comprising a light chain variable region sequence comprising SEQ ID NO:9 and a heavy chain variable region sequence comprising SEQ ID NO:10.

12. The antibody fragment of claim 11, wherein the antibody fragment is a Fab or a F(ab')2 fragment.

13. The antibody fragment of claim 11, wherein the antibody fragment is a single chain.

14. A polynucleotide compound, comprising a sequence coding for either SEQ ID NO:9 or SEQ ID NO:10 of the antibody fragment of claim 11.

15. A cell culture wherein the cultured cells express the antibody of claim 11.

16. A pharmaceutical composition, comprising the antibody fragment of claim 11 and a pharmaceutically acceptable excipient.

17. A method for increasing plasma Aβ levels or reducing brain Aβ plaque burden in a human subject, comprising administering to the human subject an effective amount of the antibody fragment of claim 11.

* * * * *

SEQUENCE LISTING

```
<160> NUMBER OF SEQ ID NOS: 20

<210> SEQ ID NO 1
<211> LENGTH: 16
<212> TYPE: PRT
<213> ORGANISM: Mus sp.

<400> SEQUENCE: 1

Lys Ser Ser Gln Ser Leu Leu Asp Ser Asp Gly Lys Thr Tyr Leu Asn
1               5                   10                  15

<210> SEQ ID NO 2
<211> LENGTH: 7
<212> TYPE: PRT
<213> ORGANISM: mus sp.

<400> SEQUENCE: 2

Leu Val Ser Lys Leu Asp Ser
1               5

<210> SEQ ID NO 3
<211> LENGTH: 9
<212> TYPE: PRT
<213> ORGANISM: mus sp.

<400> SEQUENCE: 3

Trp Gln Gly Thr His Phe Pro Arg Thr
1               5

<210> SEQ ID NO 4
<211> LENGTH: 5
<212> TYPE: PRT
<213> ORGANISM: mus sp.

<400> SEQUENCE: 4

Asn Tyr Gly Met Ser
1               5

<210> SEQ ID NO 5
<211> LENGTH: 17
<212> TYPE: PRT
<213> ORGANISM: mus sp.
```

-continued

```
<400> SEQUENCE: 5

Ser Ile Arg Ser Gly Gly Gly Arg Thr Tyr Tyr Ser Asp Asn Val Lys
1               5                   10                  15

Gly

<210> SEQ ID NO 6
<211> LENGTH: 10
<212> TYPE: PRT
<213> ORGANISM: mus sp.

<400> SEQUENCE: 6

Tyr Asp His Tyr Ser Gly Ser Ser Asp Tyr
1               5                   10

<210> SEQ ID NO 7
<211> LENGTH: 113
<212> TYPE: PRT
<213> ORGANISM: Artificial sequence
<220> FEATURE:
<223> OTHER INFORMATION: humanized antibody
<220> FEATURE:
<221> NAME/KEY: MISC_FEATURE
<222> LOCATION: (1)..(1)
<223> OTHER INFORMATION: Xaa=Asp or Tyr
<220> FEATURE:
<221> NAME/KEY: MISC_FEATURE
<222> LOCATION: (7)..(7)
<223> OTHER INFORMATION: Xaa=Ser or Thr
<220> FEATURE:
<221> NAME/KEY: MISC_FEATURE
<222> LOCATION: (10)..(10)
<223> OTHER INFORMATION: Xaa=Ser or Thr
<220> FEATURE:
<221> NAME/KEY: MISC_FEATURE
<222> LOCATION: (15)..(15)
<223> OTHER INFORMATION: Xaa=Leu, Ile, or Val
<220> FEATURE:
<221> NAME/KEY: MISC_FEATURE
<222> LOCATION: (50)..(50)
<223> OTHER INFORMATION: Xaa=Arg or Lys
<220> FEATURE:
<221> NAME/KEY: MISC_FEATURE
<222> LOCATION: (88)..(88)
<223> OTHER INFORMATION: Xaa=Val or Leu
<220> FEATURE:
<221> NAME/KEY: MISC_FEATURE
<222> LOCATION: (109)..(109)
<223> OTHER INFORMATION: Xaa=val or Leu

<400> SEQUENCE: 7

Xaa Val Val Met Thr Gln Xaa Pro Leu Xaa Leu Pro Val Thr Xaa Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Xaa Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Trp Gln Gly
                85                  90                  95

Thr His Phe Pro Arg Thr Phe Gly Gly Gly Thr Lys Xaa Glu Ile Lys
            100                 105                 110

Arg
```

<210> SEQ ID NO 8
<211> LENGTH: 119
<212> TYPE: PRT
<213> ORGANISM: Artificial sequence
<220> FEATURE:
<223> OTHER INFORMATION: humanized antibody
<220> FEATURE:
<221> NAME/KEY: MISC_FEATURE
<222> LOCATION: (3)..(3)
<223> OTHER INFORMATION: Xaa=Gln, Lys, or Arg
<220> FEATURE:
<221> NAME/KEY: MISC_FEATURE
<222> LOCATION: (78)..(78)
<223> OTHER INFORMATION: Xaa=Ser or Thr
<220> FEATURE:
<221> NAME/KEY: MISC_FEATURE
<222> LOCATION: (87)..(87)
<223> OTHER INFORMATION: Xaa=Arg or Lys
<220> FEATURE:
<221> NAME/KEY: MISC_FEATURE
<222> LOCATION: (88)..(88)
<223> OTHER INFORMATION: Xaa=Ala, Ser or Thr
<220> FEATURE:
<221> NAME/KEY: MISC_FEATURE
<222> LOCATION: (114)..(114)
<223> OTHER INFORMATION: Xaa=Leu, Thr, Ile, or Val

<400> SEQUENCE: 8

Glu Val Xaa Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Xaa Leu Tyr
65                  70                  75                  80

Leu Gln Met Asn Ser Leu Xaa Xaa Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Xaa Val Thr Val Ser Ser
        115

<210> SEQ ID NO 9
<211> LENGTH: 113
<212> TYPE: PRT
<213> ORGANISM: Artificial sequence
<220> FEATURE:
<223> OTHER INFORMATION: humanized antibody

<400> SEQUENCE: 9

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Trp Gln Gly
            85                  90                  95

Thr His Phe Pro Arg Thr Phe Gly Gly Thr Lys Val Glu Ile Lys
            100                 105                 110

Arg

<210> SEQ ID NO 10
<211> LENGTH: 119
<212> TYPE: PRT
<213> ORGANISM: Artificial sequence
<220> FEATURE:
<223> OTHER INFORMATION: humanized antibody

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
                100                 105                 110

Thr Leu Val Thr Val Ser Ser
            115

<210> SEQ ID NO 11
<211> LENGTH: 219
<212> TYPE: PRT
<213> ORGANISM: Artificial sequence
<220> FEATURE:
<223> OTHER INFORMATION: humanized antibody

<400> SEQUENCE: 11

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 12
<211> LENGTH: 449
<212> TYPE: PRT
<213> ORGANISM: Artificial sequence
<220> FEATURE:
<223> OTHER INFORMATION: humanized antibody

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Gly Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Arg Ser Gly Gly Gly Arg Thr Tyr Tyr Ser Asp Asn Val
    50                  55                  60

Lys Gly Arg Phe Thr Ile Ser Arg Glu Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Tyr Asp His Tyr Ser Gly Ser Ser Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

```
<210> SEQ ID NO 13
<211> LENGTH: 46
<212> TYPE: DNA
<213> ORGANISM: Artificial sequence
<220> FEATURE:
<223> OTHER INFORMATION: DNA primer

<400> SEQUENCE: 13
tatagagctc aagcttggat ggtgggaaga tggatacagt tggtgc                46

<210> SEQ ID NO 14
<211> LENGTH: 50
<212> TYPE: DNA
<213> ORGANISM: Artificial sequence
<220> FEATURE:
<223> OTHER INFORMATION: DNA primer

<400> SEQUENCE: 14
tatagagctc aagcttccag tggatagach gatggggstg tygttttggc            50

<210> SEQ ID NO 15
<211> LENGTH: 1953
<212> TYPE: DNA
<213> ORGANISM: Artificial sequence
<220> FEATURE:
<223> OTHER INFORMATION: humanized antibody

<400> SEQUENCE: 15
acgcgtccac catgatgagt cctgcccagt tcctgtttct gttagtgctc tggattcggg   60
aaaccaacgg tgatgttgtg atgacccagt ctccactctc cttgcctgtt acctgggac   120 aaccagcctc catctcttgc aagtcaagtc agagcctctt agatagtgat ggaaagacat  180
atttgaattg gttgcaacag cgcccaggcc agtctccaag acgcctaatc tatctggtgt  240
ctaaactgga ctctggagtc cctgacaggt tctctggcag tggatcaggg acagatttta  300
cactgaaaat cagcagagtc gaggctgagg atgtgggagt ttattattgc tggcaaggta  360 cacatttcc tcggacgttc ggtggaggca ccaaggtgga aatcaaacgt aagtgcactt  420
```

-continued

```
tccttctaga aattctaaac tctgagggg tcggatgacg tggccattct ttgcctaaag      480
cattgagttt actgcaaggt cagaaaagca tgcaaagccc tcagaatggc tgcaaagagc      540
tccaacaaaa caatttagaa ctttattaag aatagggg aagctaggaa gaaactcaaa      600
acatcaagat tttaaatacg cttcttggtc tccttgctat aattatctgg gataagcatg      660
ctgttttctg tctgtcccta acatgccctg tgattatccg caaacaacac acccaagggc      720
agaactttgt tacttaaaca ccatcctgtt tgcttctttc ctcaggaact gtggctgcac      780
catctgtctt catcttcccg ccatctgatg agcagttgaa atctggaact gcctctgttg      840
tgtgcctgct gaataacttc tatcccagag aggccaaagt acagtggaag gtggataacg      900
ccctccaatc gggtaactcc caggagagtg tcacagagca ggacagcaag acagcacct      960 acagcctcag cagcaccctg acgctgagca agcagacta cgagaaacac aaagtctacg     1020
cctgcgaagt cacccatcag ggcctgagct cgcccgtcac aaagagcttc aacaggggag     1080
agtgttagag ggagaagtgc ccccacctgc tcctcagttc cagcctgacc ccctcccatc     1140
ctttggcctc tgacccttt tccacagggg acctacccct attgcggtcc tccagctcat     1200
ctttcacctc acccccctcc tcctccttgg ctttaattat gctaatgttg gaggagaatg     1260
aataaataaa gtgaatcttt gcacctgtgg tttctctctt tcctcattta ataattatta     1320
tctgttgttt taccaactac tcaatttctc ttataaggga ctaaatatgt agtcatccta     1380
aggcgcataa ccatttataa aaatcatcct tcattctatt ttaccctatc atcctctgca     1440
agacagtcct ccctcaaacc cacaagcctt ctgtcctcac agtccctgg gccatggtag     1500 gagagacttg cttccttgtt ttcccctcct cagcaagccc tcatagtcct ttttaagggt     1560
gacaggtctt acagtcatat atcctttgat tcaattccct gagaatcaac caaagcaaat     1620
ttttcaaaag aagaaacctg ctataaagag aatcattcat tgcaacatga tataaaataa     1680
caacacaata aaagcaatta aataaacaaa caataggaa atgtttaagt tcatcatggt     1740
acttagactt aatggaatgt catgccttat ttacattttt aaacaggtac tgagggactc     1800
ctgtctgcca agggccgtat tgagtacttt ccacaaccta atttaatcca cactatactg     1860
tgagattaaa acattcatt aaaatgttgc aaaggttcta taaagctgag agacaaatat     1920
attctataac tcagcaatcc cacttctagg atc                                  1953
```

<210> SEQ ID NO 16
<211> LENGTH: 3244
<212> TYPE: DNA
<213> ORGANISM: Artificial sequence
<220> FEATURE:
<223> OTHER INFORMATION: humanized antibody

<400> SEQUENCE: 16

```
acgcgtccac catgaacttc gggctcagct tgattttcct tgtccttgtc ttaaaaggtg       60
tccagtgtga agtgcaactg gtggagtctg ggggaggctt agtgcagcct ggaggctctc      120
tgaggctctc ctgtgcaggc tctggattca ctttcagtaa ctatggcatg tcttgggttc      180
gccaggctcc tggaaaggga ctggagtggg ttgcatccat taggagtggt ggtggtagaa      240
cctactattc agacaatgta aagggccgat tcaccatctc cagagagaat gccaagaaca      300
gcctgtacct gcaaatgaac agtctgagag ctgaggacac ggctgtctat tattgtgtca      360
gatatgatca ctatagtggt agctccgact actggggcca gggcaccttg gtcacagtct      420
cctcaggtga gtcctcacaa cctctagagc tttctggggc aggccaggcc tgaccttggc      480
```

-continued

```
tttggggcag ggaggggct aaggtgaggc aggtggcgcc agccaggtgc acacccaatg    540
cccatgagcc cagacactgg acgctgaacc tcgcggacag ttaagaaccc aggggcctct    600
gcgccctggg cccagctctg tcccacaccg cggtcacatg gcaccacctc tcttgcagcc    660
tccaccaagg gcccatcggt cttcccctg gcaccctcct ccaagagcac ctctgggggc    720
acagcggccc tgggctgcct ggtcaaggac tacttccccg aaccggtgac ggtgtcgtgg    780
aactcaggcg ccctgaccag cggcgtgcac accttcccgg ctgtcctaca gtcctcagga    840
ctctactccc tcagcagcgt ggtgaccgtg ccctccagca gcttgggcac ccagacctac    900
atctgcaacg tgaatcacaa gcccagcaac accaaggtgg acaagaaagt tggtgagagg    960
ccagcacagg gagggagggt gtctgctgga agccaggctc agcgctcctg cctggacgca   1020
tcccggctat gcagcccag tccagggcag caaggcaggc cccgtctgcc tcttcacccg    1080
gaggcctctg cccgccccac tcatgctcag ggagagggtc ttctggcttt ttccccaggc   1140
tctgggcagg cacaggctag gtgcccctaa cccaggccct gcacacaaag ggcaggtgc    1200 tgggctcaga cctgccaaga gccatatccg ggaggaccct gccctgacc taagcccacc    1260 ccaaaggcca aactctccac tccctcagct cggacacctt ctctcctccc agattccagt   1320
aactcccaat cttctctctg cagagcccaa atcttgtgac aaaactcaca catgcccacc   1380
gtgcccaggt aagccagccc aggcctcgcc ctccagctca aggcgggaca ggtgccctag   1440
agtagcctgc atccagggac aggccccagc cgggtgctga cacgtccacc tccatctctt   1500
cctcagcacc tgaactcctg gggggaccgt cagtcttcct cttccccca aaacccaagg   1560 acaccctcat gatctcccgg acccctgagg tcacatgcgt ggtggtggac gtgagccacg   1620
aagaccctga ggtcaagttc aactggtacg tggacggcgt ggaggtgcat aatgccaaga   1680
caaagccgcg ggaggagcag tacaacagca cgtaccgtgt ggtcagcgtc ctcaccgtcc   1740
tgcaccagga ctggctgaat ggcaaggagt acaagtgcaa ggtctccaac aaagccctcc   1800
cagcccccat cgagaaaacc atctccaaag ccaaaggtgg acccgtgggg gtgcgagggc   1860
cacatggaca gaggccggct cggcccaccc tctgccctga gagtgaccgc tgtaccaacc   1920
tctgtcccta caggcagcc ccgagaacca caggtgtaca ccctgccccc atcccgggat   1980
gagctgacca agaaccaggt cagcctgacc tgcctggtca aaggcttcta tcccagcgac   2040
atcgccgtgg agtgggagag caatgggcag ccggagaaca actacaagac cacgcctccc   2100
gtgctggact ccgacggctc cttcttcctc tacagcaagc tcaccgtgga caagagcagg   2160
tggcagcagg ggaacgtctt ctcatgctcc gtgatgcatg aggctctgca caaccactac   2220
acgcagaaga gcctctccct gtctccgggt aaatgagtgc gacggccggc aagcccccgc   2280
tccccgggct ctcgcggtcg cacgaggatg cttggcacgt accccctgta catacttccc   2340
gggcgcccag catggaaata aagcacccag cgctgccctg ggcccctgcg agactgtgat   2400
ggttctttcc acgggtcagg ccgagtctga ggcctgagtg catgaggga ggcagagcgg    2460 gtcccactgt ccccacactg gcccaggctg tgcaggtgtg cctgggccgc ctagggtggg   2520
gctcagccag gggctgccct cggcaggtg ggggatttgc cagcgtggcc ctccctccag    2580
cagcacctgc cctgggctgg gccacgggaa gccctaggag ccctggggga cagacacaca   2640 gccctgcct ctgtaggaga ctgtcctgtt ctgtgagcgc cctgtcctcc gacctccatg    2700
cccactcggg ggcatgccta gtccatgtgc gtaggacag gccctccctc acccatctac   2760
ccccacggca ctaaccctg gctgccctgc ccagcctcgc acccgcatgg ggacacaacc   2820
gactccgggg acatgcactc tcgggccctg tggagggact ggtgcagatg cccacacaca   2880
```

```
cactcagccc agacccgttc aacaaacccc gcactgaggt tggccggcca cacggccacc    2940
acacacacac gtgcacgcct cacacacgga gcctcacccg ggcgaactgc acagcaccca    3000
gaccagagca aggtcctcgc acacgtgaac actcctcgga cacaggcccc cacgagcccc    3060
acgcggcacc tcaaggccca cgagcctctc ggcagcttct ccacatgctg acctgctcag    3120
acaaacccag ccctcctctc acaagggtgc cctgcagcc gccacacaca cagggggat     3180 cacacaccac gtcacgtccc tggccctggc ccacttccca gtgccgccct tccctgcagg    3240
atcc                                                                  3244
```

<210> SEQ ID NO 17
<211> LENGTH: 717
<212> TYPE: DNA
<213> ORGANISM: Artificial sequence
<220> FEATURE:
<223> OTHER INFORMATION: humanized antibody

<400> SEQUENCE: 17

```
atgatgagtc ctgcccagtt cctgtttctg ttagtgctct ggattcggga aaccaacggt      60
gatgttgtga tgacccagtc tccactctcc ttgcctgtta ccctgggaca accagcctcc     120
atctcttgca gtcaagtca gagcctctta gatagtgatg aaagacata tttgaattgg       180 ttgcaacagc gcccaggcca gtctccaaga cgcctaatct atctggtgtc taaactggac    240
tctggagtcc ctgacaggtt ctctggcagt ggatcaggga cagattttac actgaaaatc    300
agcagagtcg aggctgagga tgtgggagtt tattattgct ggcaaggtac acattttcct    360
cggacgttcg gtggaggcac caaggtggaa atcaaacgta ctgtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgt      717
```

<210> SEQ ID NO 18
<211> LENGTH: 1404
<212> TYPE: DNA
<213> ORGANISM: Artificial sequence
<220> FEATURE:
<223> OTHER INFORMATION: humanized antibody

<400> SEQUENCE: 18

```
atgaacttcg gctcagctt gatttccctt gtccttgtct taaaaggtgt ccagtgtgaa     60
gtgcaactgg tggagtctgg gggaggctta gtgcagcctg gaggctctct gaggctctcc    120
tgtgcaggct ctggattcac tttcagtaac tatggcatgt cttgggttcg ccaggctcct    180
ggaaagggac tggagtgggt tgcatccatt aggagtggtg gtggtagaac ctactattca    240
gacaatgtaa aggccgatt caccatctcc agagagaatg ccaagaacag cctgtacctg    300
caaatgaaca gtctgagagc tgaggacacg gctgtctatt attgtgtcag atatgatcac    360
tatagtggta gctccgacta ctggggccag ggcaccttgg tcacagtctc ctcagcctcc    420
accaagggcc catcggtctt ccccctggca ccctcctcca agagcacctc tgggggcaca    480
gcggccctgg gctgcctggt caaggactac ttccccgaac cggtgacggt gtcgtggaac    540
tcaggcgccc tgaccagcgg cgtgcacacc ttcccggctg tcctacagtc ctcaggactc    600
```

```
tactccctca gcagcgtggt gaccgtgccc tccagcagct tgggcaccca gacctacatc    660
tgcaacgtga atcacaagcc cagcaacacc aaggtggaca gaaagttgag cccaaatct     720 tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga tgagctgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaa                                          1404
```

<210> SEQ ID NO 19
<211> LENGTH: 239
<212> TYPE: PRT
<213> ORGANISM: Artificial sequence
<220> FEATURE:
<223> OTHER INFORMATION: humanized antibody

<400> SEQUENCE: 19

```
Met Met Ser Pro Ala Gln Phe Leu Phe Leu Leu Val Leu Trp Ile Arg
1               5                   10                  15

Glu Thr Asn Gly Asp Val Val Met Thr Gln Ser Pro Leu Ser Leu Pro
            20                  25                  30

Val Thr Leu Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Gln Gln Arg
    50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Arg Thr Phe Gly Gly Gly Thr Lys
        115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220
```

```
Gly Leu Ser Ser Pro Val Thr Lys Ser Phe Asn Arg Gly Glu Cys
225                 230                 235
```

<210> SEQ ID NO 20
<211> LENGTH: 468
<212> TYPE: PRT
<213> ORGANISM: Artificial sequence
<220> FEATURE:
<223> OTHER INFORMATION: humanized antibody

<400> SEQUENCE: 20

```
Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Gly Ser Gly Phe Thr Phe
        35                  40                  45

Ser Asn Tyr Gly Met Ser Trp Val Arg Gln Ala Pro Gly Lys Gly Leu
    50                  55                  60

Glu Trp Val Ala Ser Ile Arg Ser Gly Gly Arg Thr Tyr Tyr Ser
65                  70                  75                  80

Asp Asn Val Lys Gly Arg Phe Thr Ile Ser Arg Glu Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Val Arg Tyr Asp His Tyr Ser Gly Ser Ser Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350
```

-continued

```
Ile Glu Lys Thr Ile Ser Lys Ala Lys Gly Gln Pro Arg Glu Pro Gln
    355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465
```